(12) United States Patent
Bono et al.

(10) Patent No.: US 11,224,484 B2
(45) Date of Patent: Jan. 18, 2022

(54) SURGICAL SENSOR ANCHOR SYSTEM

(71) Applicant: GLOBUS MEDICAL, INC., Audubon, PA (US)

(72) Inventors: Peter L. Bono, Bingham Farms, MI (US); James D. Lark, West Bloomfield, MI (US); John S. Scales, Ann Arbor, MI (US); Thomas J. Lord, South Milwaukee, WI (US)

(73) Assignee: Globus Medical Inc., Audubon, PA (US)

( * ) Notice: Subject to any disclaimer, the term of this patent is extended or adjusted under 35 U.S.C. 154(b) by 0 days.

(21) Appl. No.: 16/246,291

(22) Filed: Jan. 11, 2019

(65) Prior Publication Data

US 2019/0216560 A1 Jul. 18, 2019

Related U.S. Application Data

(60) Provisional application No. 62/616,673, filed on Jan. 12, 2018, provisional application No. 62/681,462, (Continued)

(51) Int. Cl.
*A61B 90/00* (2016.01)
*A61B 34/20* (2016.01)
(Continued)

(52) U.S. Cl.
CPC .......... *A61B 34/20* (2016.02); *A61B 17/8875* (2013.01); *A61B 34/30* (2016.02); *A61B 34/76* (2016.02); *A61B 90/361* (2016.02); *A61B 90/39* (2016.02); *A61B 17/68* (2013.01); *A61B 17/864* (2013.01); *A61B 17/8605* (2013.01); *A61B 34/35* (2016.02); *A61B 2034/2048* (2016.02); *A61B 2034/2051* (2016.02); *A61B 2034/2055* (2016.02); *A61B 2034/305* (2016.02); *A61B 2090/397* (2016.02); *A61B 2090/3958* (2016.02); *A61B 2090/3983* (2016.02); *A61B 2090/3987* (2016.02);
(Continued)

(58) Field of Classification Search
None
See application file for complete search history.

(56) References Cited

U.S. PATENT DOCUMENTS 5,383,454 A 1/1995 Bucholz
5,445,166 A 8/1995 Taylor
(Continued)

FOREIGN PATENT DOCUMENTS

| WO | WO0130257 | 5/2001 |
|---|---|---|
| WO | WO2005084572 | 9/2005 |
| WO | WO2017064254 | 4/2017 |

*Primary Examiner* — Luther Behringer

(57) ABSTRACT

Surgical systems for use in surgical procedures utilizing robotic devices. The surgical system having one or more components for housing a sensor or one or more tools for anchor or sensor delivery. The surgical system may include a surgical sensor anchor and/or a surgical sensor anchor delivery tool. A method of performing a robotically assisted surgical procedure, comprising using a surgical sensor anchor during a surgical procedure which utilizes a robot to track movement of at least one portion of a body structure undergoing a surgical procedure or to track movement of a body structure near a surgical site.

22 Claims, 37 Drawing Sheets

Related U.S. Application Data filed on Jun. 6, 2018, provisional application No. 62/754,754, filed on Nov. 2, 2018.

(51) Int. Cl.
| | | |
|---|---|---|
| *A61B 34/30* | (2016.01) | |
| *A61B 17/88* | (2006.01) | |
| *A61B 34/00* | (2016.01) | |
| *A61B 17/86* | (2006.01) | |
| *A61B 34/35* | (2016.01) | |
| *A61B 17/68* | (2006.01) | |

(52) U.S. Cl.
CPC ............... *A61B 2090/3991* (2016.02); *A61B 2090/3995* (2016.02); *A61B 2562/0204* (2013.01); *A61B 2562/0219* (2013.01); *A61B 2562/0223* (2013.01)

(56) References Cited

U.S. PATENT DOCUMENTS

| | | |
|---|---|---|
| 5,891,034 A | 4/1999 | Bucholz |
| 6,611,141 B1 | 8/2003 | Shultz et al. |
| 7,007,699 B2 * | 3/2006 | Martinelli ............... A61B 90/39 128/899 |
| 7,727,235 B2 * | 6/2010 | Contiliano ......... A61B 17/0401 606/86 A |
| 7,835,778 B2 * | 11/2010 | Foley ................. A61B 17/1757 600/407 |
| 7,885,701 B2 | 2/2011 | DiSilvestro et al. |
| 7,899,226 B2 | 3/2011 | Pescatore et al. |
| 8,086,026 B2 | 12/2011 | Shultz |
| 8,206,405 B2 | 6/2012 | Beverland et al. |
| 8,213,693 B1 | 7/2012 | Li |
| 8,287,522 B2 | 10/2012 | Moses et al. |
| 8,357,165 B2 | 1/2013 | Grant et al. |
| 9,492,241 B2 | 11/2016 | Joskowicz et al. |
| 9,561,387 B2 | 2/2017 | Yan et al. |
| 9,675,272 B2 | 6/2017 | Selover et al. |
| 9,782,229 B2 * | 10/2017 | Crawford ............. A61B 17/025 |
| 9,895,559 B2 | 2/2018 | Chang et al. |
| 9,901,400 B2 | 2/2018 | Gowda et al. |
| 9,921,276 B2 | 3/2018 | Frigg et al. |
| 9,964,649 B2 | 5/2018 | Shafer et al. |
| 2002/0183608 A1 | 12/2002 | Marmulla et al. |
| 2003/0066538 A1 * | 4/2003 | Martinelli ............... A61B 90/39 128/899 |
| 2007/0010820 A1 * | 1/2007 | Contiliano ......... A61B 17/0401 606/86 A |
| 2008/0269596 A1 * | 10/2008 | Revie .................... A61F 2/4603 600/424 |
| 2010/0191071 A1 | 7/2010 | Anderson et al. |
| 2012/0201421 A1 | 8/2012 | Hartman et al. |
| 2013/0345718 A1 * | 12/2013 | Crawford ............. A61B 17/025 606/130 |
| 2015/0257851 A1 | 9/2015 | Plassky et al. |
| 2016/0151120 A1 | 6/2016 | Kostrzewski et al. |
| 2016/0242849 A9 | 8/2016 | Crawford et al. |
| 2017/0079723 A1 | 3/2017 | Fleig et al. |
| 2017/0231709 A1 | 8/2017 | Gupta et al. |
| 2017/0312033 A1 | 11/2017 | Huang et al. |

* cited by examiner

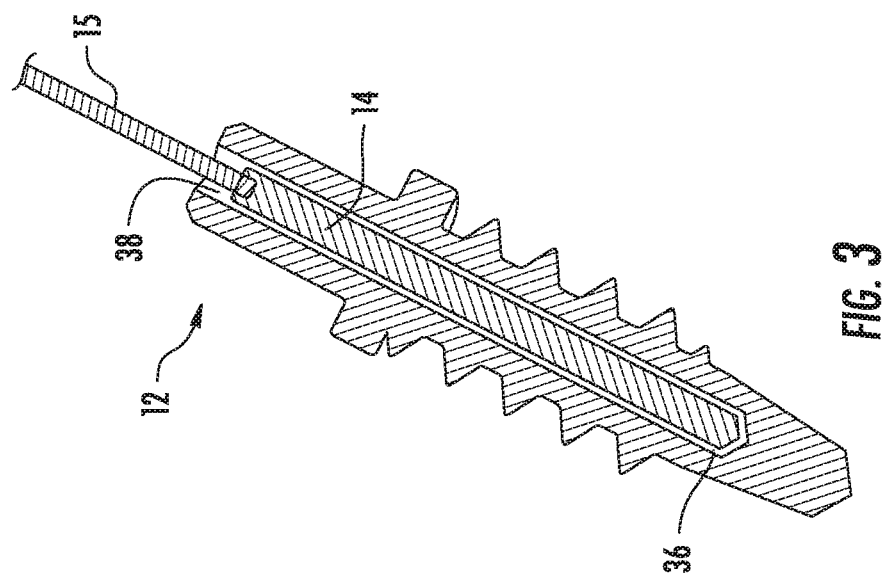
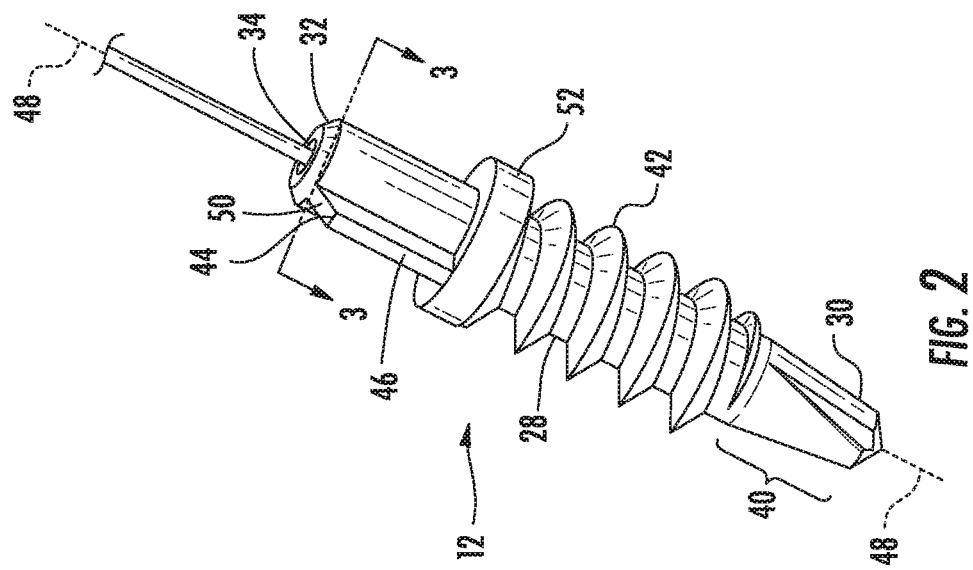

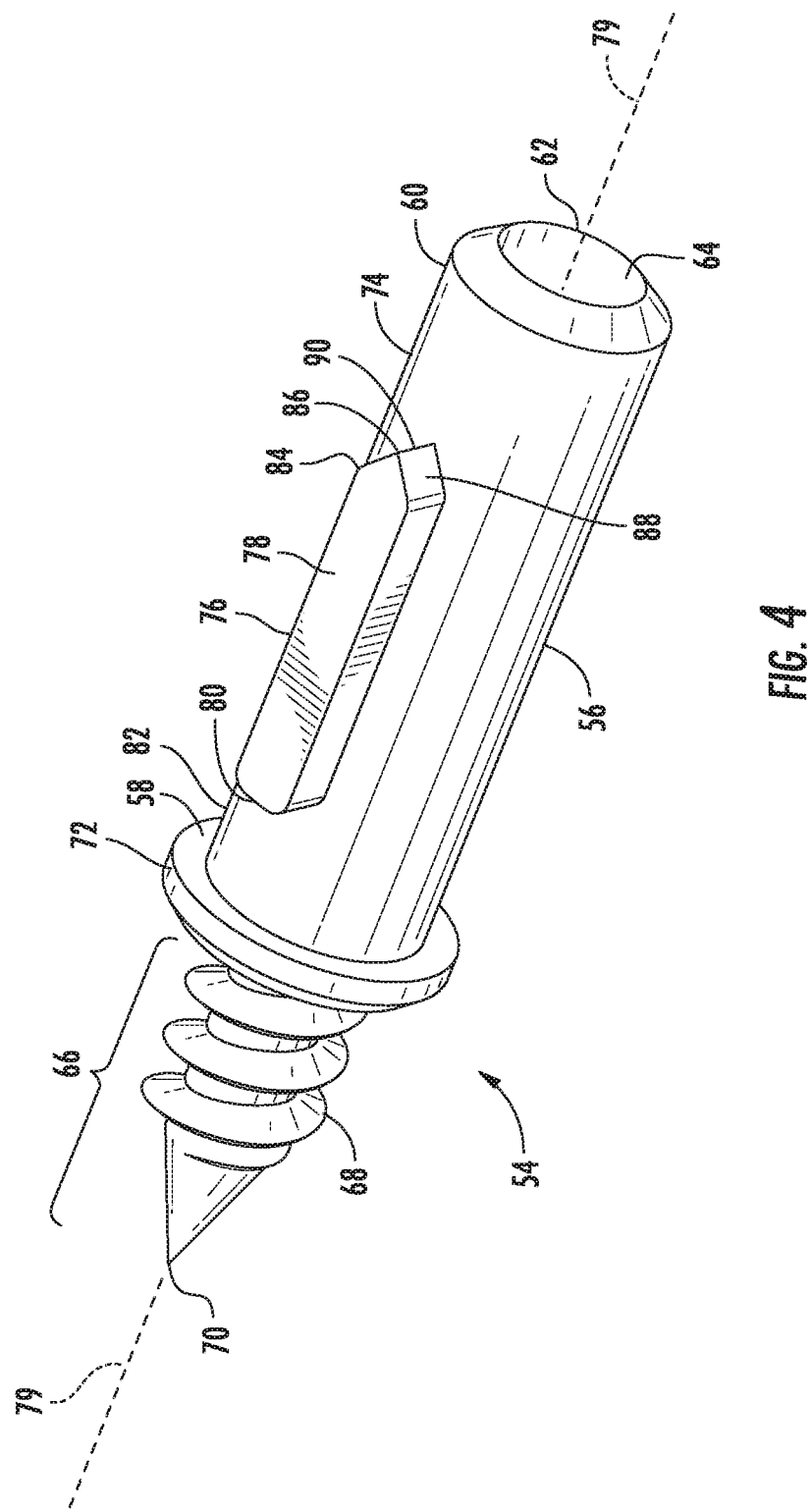

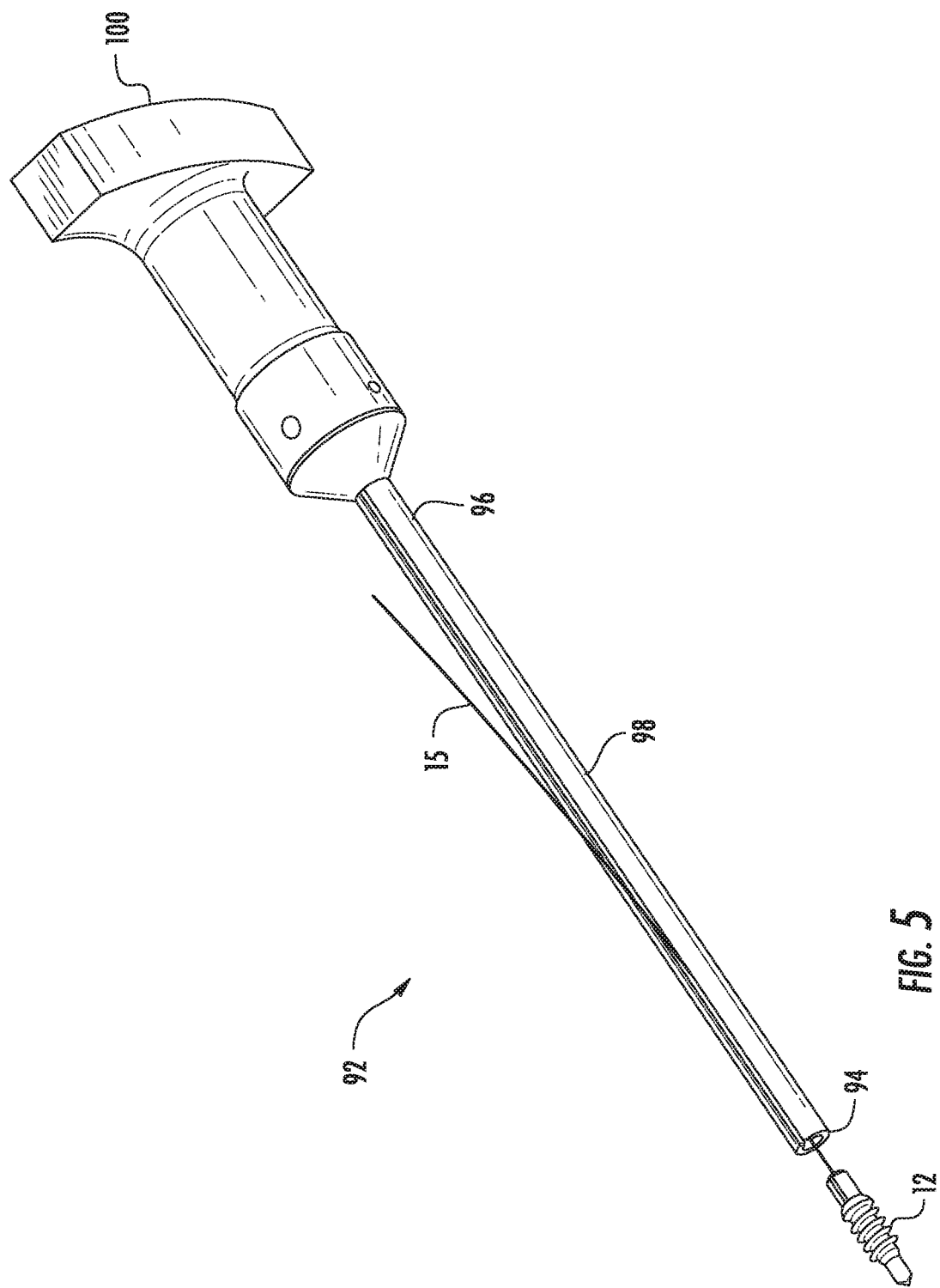

SURGICAL SENSOR ANCHOR SYSTEM

CROSS REFERENCE

In accordance with 37 C.F.R. 1.76, a claim of priority is included in an Application Data Sheet filed concurrently herewith. Accordingly, the present invention claims priority under 35 U.S.C. § 119(e), 120, 121, and/or 365(c) to U.S. Provisional Application No. 62/616,673, entitled "SURGICAL SENSOR ANCHOR SYSTEM", filed Jan. 12, 2018; to U.S. Provisional Application No. 62/681,462, entitled "SURGICAL SENSOR ANCHOR SYSTEM", filed Jun. 6, 2018; and to U.S. Provisional Application No. 62/754,754, entitled "ROBOTIC SURGICAL SYSTEM", filed Nov. 2, 2018. The contents of the above referenced applications are incorporated herein by reference in its entirety.

FIELD OF THE INVENTION

The present invention relates to surgical systems and robot-assisted surgical methods; and more particularly, to a surgical sensor anchor system for use in surgical procedures utilizing robotic devices, and methods of performing a robotically assisted surgical procedure, the system and methods having one or more components for housing a sensor, a sensor anchor, and one or more tools for anchor or sensor delivery.

BACKGROUND OF THE INVENTION

Surgical procedures, such as those performed on the spine, are well known in the art. The central nervous system is a vital part of the human physiology that coordinates human activity. It is primarily made up of the brain and the spinal cord. The spinal cord is made up of a bundle of nerve tissue which originates in the brain and branches out to various parts of the body, acting as a conduit to communicate neuronal signals from the brain to the rest of the body, including motor control and sensations. Protecting the spinal cord is the spinal, or vertebral, column. Anatomically, the spinal column is made up of several regions, including the cervical, thoracic, lumbar and sacral regions. Each of the vertebrae associated with the various spinal cord regions are made up of a vertebral body, a posterior arch, and transverse processes.

While most people have fully functional spinal cords, it is not uncommon for individuals to suffer some type of spinal ailment or disorder which requires some type of surgical intervention. There are many different approaches taken to alleviate or minimize severe spinal disorders. One surgical procedure commonly used is a spinal fusion technique. Several surgical approaches have been developed over the years, and include the Posterior Lumbar Interbody Fusion (PLIF) procedure which utilizes a posterior approach to access the patient's vertebrae or disc space, the Transforaminal Lumbar Interbody Fusion (TLIF) procedure which utilizes a posterior and lateral approach to access the patient's vertebrae or disc space, and the Anterior Lumbar Interbody Fusion (ALIF) which utilizes an anterior approach to access the patient's vertebrae or disc space. Using any of these surgical procedures, the patient undergoes spinal fusion surgery in which two or more vertebrae are linked or fused together through the use of a bone spacing device and/or use of bone grafts. The resulting surgery eliminates any movement between the spinal sections which have been fused together.

In addition to the spinal implants or use of bone grafts, spinal fusion surgery often utilizes spinal instrumentation or surgical hardware, such as pedicle screws, plates, or spinal rods. Once the spinal spacers and/or bone grafts have been inserted, a surgeon places the pedicle screws into a portion of the spinal vertebrae and attaches either rods or plates to the screws as a means for stabilization while the bones fuse. Currently available systems for inserting the rods into pedicle screws can be difficult to use, particularly in light of the fact that surgeons installing these rods often work in narrow surgical fields.

Moreover, since patients can vary with respect to their internal anatomy, resulting in varying curvatures of the spine, a surgeon may not always have a linear path, or may have anatomical structures that must be maneuvered around in order to properly insert the surgical rods into the pedicle screw assemblies. In addition to requiring surgical skill, difficulty in placing the rods correctly into the pedicle screws can result in unnecessary increases in the time it takes a surgeon to complete the surgical procedure. Prolonged surgery times increase the risk to the patient. More importantly, improperly aligning the rods and pedicle screw assemblies often results in post-surgery complications for the patient and requires corrective surgical procedures.

Surgery is often required to repair broken skeletal components. Some bones are easier to put into place for healing than others. For example, a pelvis is plate like, having a large surface area for a given volume and, when broken, can have multiple fragments that need to be reassembled in place so that the bone fragments can grow back together. Skulls also have plate like configuration. This is unlike setting a femur or the like, since they typically do not fragment. Further, when a large surface area bone such as the pelvis or skull breaks into multiple fragments, it is difficult to determine where a particular fragment goes; and, if the trauma to the body is severe, the fragments can move about and not be in the same orientation they were in before breaking. Such breaking can occur in car accidents, falls and industrial accidents. It is left up to the skill of the surgeon to determine where a fragment goes and its orientation relative to other fragments. It is often difficult for a surgeon to hold these bone fragments in place to secure them in their proper orientation as with plates, screws, adhesives or the like. The more fragments, the more difficult the surgeon's job is. To further complicate such reconstruction, time spent doing the surgery should be as short as possible to help avoid surgical complications. Generally, the longer the surgical procedure, the higher the risk to the patient. Additionally, the more fragments, the more hands are needed to effect the reconstruction. The more human hands participating, the more difficult the surgery from a space standpoint.

In addition to requiring surgical skill, difficulty in placing the fragments can result in unnecessary increases in the time it takes a surgeon to perform the surgical procedure. Prolonged surgery times increase the risk to the patient. More importantly, improperly alignment of the fragments or placing them in an incorrect position can result in post-surgery complications for the patient and might require complex corrective surgical procedures later.

Robotic surgery, computer-assisted surgery, and robotically-assisted surgery are terms for technological developments that use robotic systems to aid in surgical procedures. Robotically-assisted surgery was developed to overcome the limitations of pre-existing minimally-invasive surgical procedures and to enhance the capabilities of surgeons performing open surgery.

In the case of robotically-assisted minimally-invasive surgery, instead of directly moving the instruments, the surgeon uses one of two methods to control the instruments; either a direct telemanipulator or through computer control. A telemanipulator is a remote manipulator that allows the surgeon to perform the normal movements associated with the surgery while the robotic arms carry out those movements using end-effectors and manipulators to perform the actual surgery on the patient. In computer-controlled systems, the surgeon uses a computer to control the robotic arms and its end-effectors, though these systems can also still use telemanipulators for their input. One advantage of using the computerized method is that the surgeon does not have to be present, but can be anywhere in the world, leading to the possibility for remote surgery. One drawback relates to the lack of tactile feedback to the surgeon. Another drawback relates to visualization of the surgical site. Because the surgeon may be remote or the surgery may be percutaneous, is it difficult for the surgeon to view the surgery as precisely as may be needed.

In the case of enhanced open surgery, autonomous instruments (in familiar configurations) replace traditional steel tools, performing certain actions (such as rib spreading) with much smoother, feedback-controlled motions than could be achieved by a human hand. The main object of such smart instruments is to reduce or eliminate the tissue trauma traditionally associated with open surgery.

While robots are fully capable of repetitive tasks and work well in planned, routine settings, such environments are not always possible during a surgical procedure. In addition, robots are unintelligent in that they must be programmed to perform their functionality. However, this can be problematic when the environments they are programmed to function in are not static. As robotic systems become more prevalent in the surgical field, there exists a need for such robotic-assisted procedures to be performed safely and more intelligently, and capable of modifications in real time.

SUMMARY OF THE INVENTION

The present invention provides apparatus, systems, and methods for use with robotically assisted surgery. The invention provides a surgical sensor anchor system for use in surgical procedures utilizing robotic devices. The invention further provides methods of performing a robotically assisted surgical procedure. The system and method utilizes a surgical sensor anchor having a sensor for use in tracking movement of at least one portion of a body structure undergoing a surgical procedure, or tracking movement of a body structure near a surgical site. The tracked movement can then be used to adjust directions of the robot in real time.

The present invention further provides apparatus, systems, and methods for use with robotically assisted surgery. The invention provides a robotic system and surgical sensor anchor system for use in surgical procedures utilizing one or more robotic devices. The invention further provides methods of performing a robotically assisted skeletal surgical procedure. The system and method can utilize a surgical sensor anchor having a sensor for use in tracking movement of at least one portion of a body structure undergoing a surgical procedure, effecting movement of a body structure near a surgical site and retaining it in a selected location for reconnection. The body structure movement can be manually controlled and/or robotically controlled in real time. The invention is particularly useful in orthopedic skeletal surgery.

Accordingly, it is an objective of the invention to provide a system for use with robotically assisted surgery.

It is an objective of the invention to provide a system for use with robotically assisted surgery where the robot can be used manually and with a controller.

It is a further objective of the invention to provide methods for use with robotically assisted surgery.

It is yet another objective of the invention to provide a surgical sensor anchor system for use in surgical procedures utilizing robotic devices.

It is a still further objective of the invention to provide methods of performing a robotically assisted surgical procedure using one or more robots.

It is a still further objective of the invention to provide methods of performing a robotically assisted surgical procedure.

It is a further objective of the invention to provide a system that utilizes a surgical sensor anchor having a sensor for use in tracking movement of at least one portion of a body structure undergoing a surgical procedure or tracking movement of a body structure near a surgical site.

It is yet another objective of the invention to provide a system that utilizes tracked movement to adjust directions of the robot during a surgical procedure in real time.

It is yet another objective of the invention to provide a method of performing a robotically assisted surgical procedure that utilizes a surgical sensor anchor having a sensor for use in tracking movement of at least one portion of a body structure undergoing a surgical procedure or tracking movement of a body structure near a surgical site.

It is a still further objective of the invention to provide a method of performing a robotically assisted surgical procedure that utilizes tracked movement to adjust directions of the robot during a surgical procedure in real time.

It is an even further objective of the invention to provide a redundant monitoring system that utilizes at least two types of fiducial markers.

Still yet a further objective of the invention is to provide a monitoring system that utilizes electromagnetic as well as optical sensors to monitor the position of a body structure.

It is yet another objective of the invention to provide a method of performing a robotically assisted surgical procedure that utilizes a surgical sensor anchor having a sensor for identifying a skeletal part and tracking movement of at least one portion of a skeletal part undergoing a surgical procedure.

It is a still further objective of the invention to provide a method of performing a robotically assisted surgical procedure that utilizes tracked movement and/or skeletal part orientation to adjust directions of the robot during a surgical procedure in real time.

Still yet a further objective of the invention is to provide a monitoring system that utilizes electromagnetic as well as optical sensors to monitor the position and orientation of a skeletal part relative to other skeletal parts.

It is even a further objective of the invention to program a computer to control movements of one or more robots used in the surgery.

It is a still further objective of the invention to program a computer and connect it to a vision system to identify skeletal parts and have the computer identify their positional relationship to at least one of the body structure parts, and optionally control movement of at least one of the parts by a surgical robot to position the part for reassembly.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

FIG. 2 is a perspective view of an illustrative embodiment of a surgical sensor anchor for use in a surgical procedure, configured for receiving and storing therein a sensor;

FIG. 3 is a cross section view of the surgical sensor anchor shown in FIG. 2, taken along lines 3-3;

FIG. 4 is a perspective view of an alternative embodiment of the surgical sensor anchor for use in a surgical procedure, configured for receiving and storing therein a sensor;

FIG. 5 is an illustrative example of an anchor delivery tool;

DETAILED DESCRIPTION OF THE INVENTION

Figure 1:
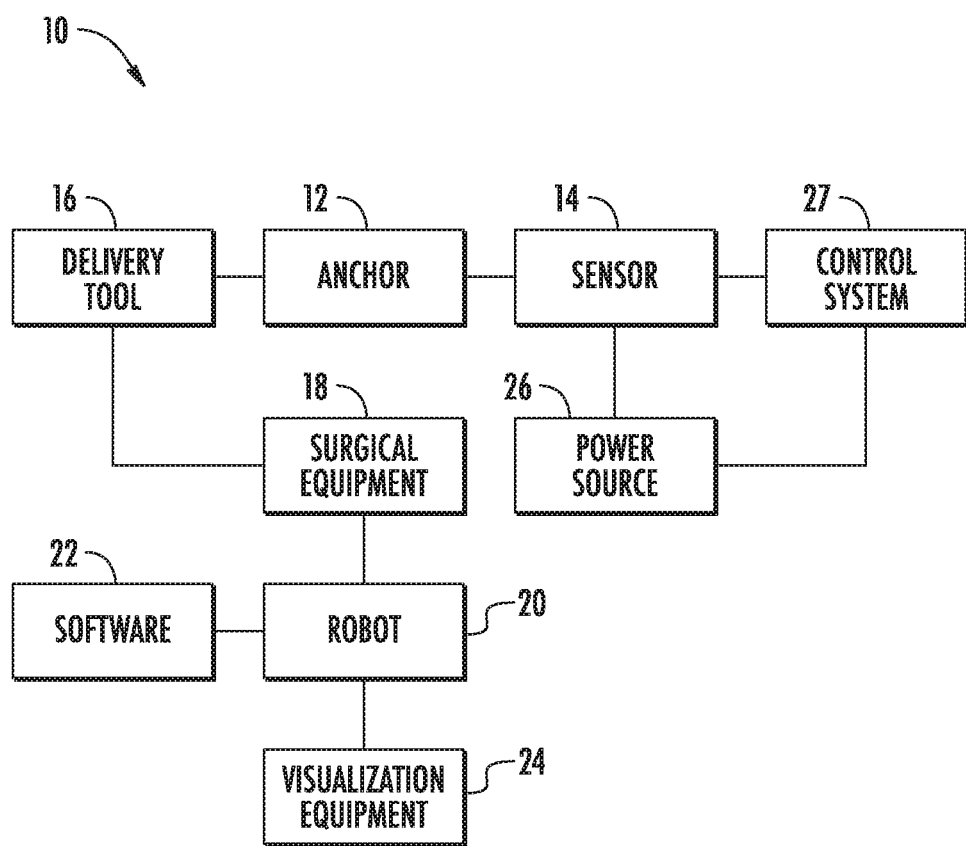
FIG. 1 is a block diagram of an illustrative embodiment of a surgical sensor anchor system.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Referring to FIG. 1, a schematic, block diagram illustration of a system, referred to generally as a surgical sensor anchor system 10 is illustrated. The surgical sensor anchor system 10 may comprise of any one element alone, or any two or more components in combination. The surgical sensor anchor system 10 is comprised of a surgical anchor 12, a sensor 14, an anchor delivery tool 16, surgical equipment, such as a surgical robot 20 with software 22 to drive robotic functionality, and visualizing equipment 24, such as a CT scan, ultrasound or fluoroscopy, and a sensor power source 26 and sensor control system 27.

In use, the system and methods provide a mechanism for a safer and controlled robotically-assisted surgical procedure, as the robot will be able to respond to changes in the surgical environment and modify its programmed actions.

This will be beneficial in the situation where a patient's body, and therefore the surgical site, is moved during a surgical procedure. When undertaken by a human, such action is not problematic, as humans have the capability to problem solve in real time. That is, the surgeon understands and processes that the body is moved and either moves it back or continues on the path knowing that the body is positioned differently. For a robot that is programmed to do an action, it does not understand such action and will continue to do what it is programmed to do, regardless of where the surgical site has been placed. This continued path can result in incomplete actions, or more importantly, performing an action on the wrong surgical site or body part/portion. Accordingly, if the body shifts, it would be necessary to stop the procedure and reprogram the robot pathway, resulting in increased surgical times and possible mistakes.

As an illustrative example, the sensor 14 may be an electromagnetic sensor which can be temporarily attached to at least one portion of a body structure undergoing a surgical procedure or tracking movement of a body structure near a surgical site. For example, the surgical anchor 12 having a sensor 14 (or surgical sensor anchor 54/354 to be described later) may be temporarily fixed to each vertebra level during a spinal surgery. In a three-level fusion procedure, the surgeon temporarily anchors in three (3) separate surgical anchors 12 having a sensor 14 (or surgical sensor anchor 54 or 354) at each level. The sensor may be used with an electromagnetic tracking system (see NDI Medical (Ontario, Canada) electromagnetic tracking system). In the utilization of the temporary sensors, i.e. sensor anchor 12/54/354 with sensor 14 on each vertebra level, the surgeon would provide an initial registration to plot the robot pathway using ultrasound or other known methods. Once the robot path system is determined and programmed, each sensor would be turned on during cutting, drilling, and screwing into that particular level. The sensor would preferably track six degrees of freedom, i.e. in spinal procedure, flexion, extension, axial rotation, latero-lateral shear, anteroposterior shear, axial compression/decompression, and track any movement of the vertebra, providing feedback to the robot. The feedback information would then be used by the robot to adjust direction in real-time, or act accordingly, such as stopping the surgical procedure until human input is performed.

The sensor 14 can be an electromagnetic sensor which can be temporarily attached to at least one portion of a skeletal structure undergoing a surgical procedure or tracking movement of a skeletal part near a surgical site. For example, the surgical anchor 12 having a sensor 14 (or surgical sensor anchor 54/354 to be described later) may be temporarily fixed to a skeletal part during surgery as with a screw threaded portion. In a pelvis reconstruction procedure, the surgeon temporarily anchors in the appropriate number of surgical anchors 12, optionally having a sensor 14 (or surgical sensor anchor 54 or 354) at each level, into the skeletal parts to be repositioned for reconstruction, i.e., to assemble the broken parts back into as near a whole pelvis 13 as practicable. While the term pelvis is used herein, it is to be understood that other skeletal components can be treated with the herein described system and method, and in particular, plate like components including the pelvis and skull. The sensor 14 may be used with an electromagnetic tracking system (see NDI Medical (Ontario, Canada) electromagnetic tracking system). In the utilization of the sensors 14, i.e. sensor anchor 12, 54, 354 with sensor 14 on each skeletal part, the surgeon would provide an initial registration to plot the robot pathway using ultrasound or other known methods. Once the robot path system is determined and programmed, each sensor 14 would be turned on during the surgical procedure. The sensor(s) 14 would preferably track six degrees of freedom, i.e. in the reconstruction procedure, providing feedback to the robot to either move a particular skeletal part or to hold it in position for securement in proper place. The feedback information could also be used by the robot to adjust position or movement in real-time, or act accordingly, such as stopping the surgical procedure until human input is performed. The visualization system 24, described in more detail below, can also be used to track movement of the various skeletal portions 1201A-1201D of a broken pelvis 13.

Referring to FIGS. 2 and 3, an illustrative embodiment of a surgical anchor 12 for use in a surgical procedure and configured to house a sensor therein, referred to generally as a surgical anchor 12, is illustrated. The surgical anchor 12 comprises a main body 28 having a first end 30 configured to engage with a body part or organ, such as a vertebra, and an opposing second end 32 positioned away from the body part when inserted therein. While the main body 28 is shown having a generally tubular shape, such shape is illustrative only and not limiting. The second end 32 contains an opening 34. The opening 34 preferably has a diameter sufficient to allow the sensor 14 (shown with an electrical wire 15) to be inserted into and stored within a lumen 36 in the interior region 38 of the surgical anchor 12.

The first end 30 of the surgical anchor 12 may contain an initial insertion portion 40 constructed to aid in insertion into, for example, a vertebra. The partially threaded portion 42 allows the surgical anchor 12 to be screwed into and thereby secured to the vertebra. Positioned at or near the second end 32 is an insertion tool engaging member 44. The insertion tool engaging member 44 is illustrated herein as an elongated flange 46 arranged in a generally parallel orientation relative to the anchor longitudinal axis 48 and extending inwardly towards a center of the surgical anchor 12. The elongated flange 46 may comprise an angled or ramped surface 50 for guiding an insertion tool at one end, and end in a circumferential flange 52. The circumferential flange 52 is illustrated having a generally circular shape or profile and extending around a perimeter of the anchor 12 main body 28.

FIG. 4 illustrates an alternative embodiment of the anchor for use in a surgical procedure and configured to house a sensor therein, referred to generally as a surgical sensor anchor 54. The surgical sensor anchor 54 comprises a main body 56 having a first end 58 configured to engage with a body part or organ, such as a vertebra, and an opposing second end 60 positioned away from the body part when inserted therein. While the main body 56 is shown having a generally tubular shape, such shape is illustrative only and not limiting. The second end 60 contains an opening 62. The opening 62 preferably has a diameter sufficient to allow the sensor 14 to be inserted into and stored within an interior region 64 of the surgical sensor anchor 54. The first end 58 of the surgical sensor anchor 54 may contain an initial insertion portion 66 constructed to aid in insertion into, for example, a vertebra. A threaded portion 68 allows the surgical sensor anchor 54 to be screwed into and secured to the vertebra. The insertion portion 66 terminates in an initial body part engaging portion, illustrated herein as a sharp or pointed tip 70. At, near, or extending from the first end 58, preferably prior to the threaded portion 68, is a circumferential flange 72. The circumferential flange 72 is illustrated having a generally circular shape or profile and extending around a perimeter of the surgical sensor anchor 54 main body 56.

Positioned along the outer surface 74 of the main body 56 is an insertion tool engaging member 76. The insertion tool engaging member 76 is illustrated herein as an elongated body or flange 78 extending out from the outer surface 74 and arranged in a generally parallel orientation relative to the surgical anchor longitudinal axis 79. The elongated body or flange 78 may comprise a first end 80, shown having a generally rounded 82 profile, and a second, opposing end 84, having a partial triangular profile with two surfaces 86 and 88 diverging from an edge or edge surface 90. While the anchors 12, 54 (and 354) are shown as using a threaded shank to effect attachment to a skeletal component, it is to be understood that other forms of attachment can be used, such as adhesive attachment.

Figure 6:
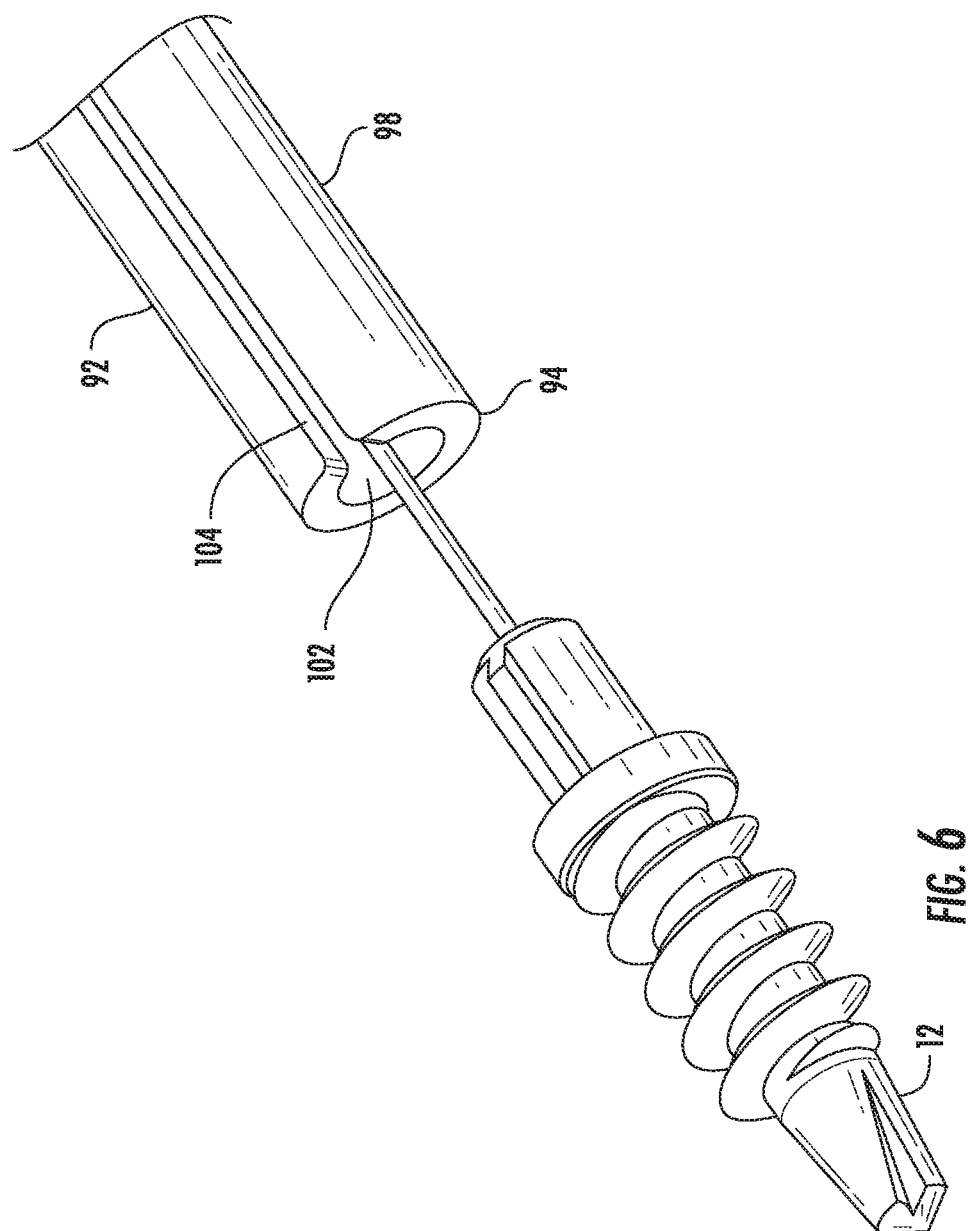
FIG. 6 is a partial view of the anchor delivery tool shown in FIG. 5, illustrating the portion of the tool that engages with the anchor.

FIG. 5 illustrates an embodiment of an anchor delivery tool, referred to generally as a surgical anchor insertion tool 92 configured to engage with the surgical sensor anchor 12 or 54 (or 354), delivering the surgical sensor anchor 12 or 54 (or 354) to the required portion of the body in need of a surgical procedure. The surgical anchor insertion tool 92 comprises a first end 94, configured to engage with the surgical sensor anchor 12 or 54 (or 354), a second end 96, and a main body shaft 98. A handle 100, shown as a T-shaped handle, is attached to or integrally formed to the second end 96. As illustrated in FIG. 6, the first end 94 has an opening 102 sized and shaped to receive and secure at least a portion of the surgical anchor 12 (54, 354). The first end 94 comprises a slotted opening 104 running along the length of the shaft. The length of the slotted opening 104 is larger than the insertion tool engaging member 44/76 so the insertion tool engaging member 44/76 fits therein. The slotted opening 104 also allows the electrical wire 15 of the sensor 14 to be inserted into and rest therein.

Figure 7:
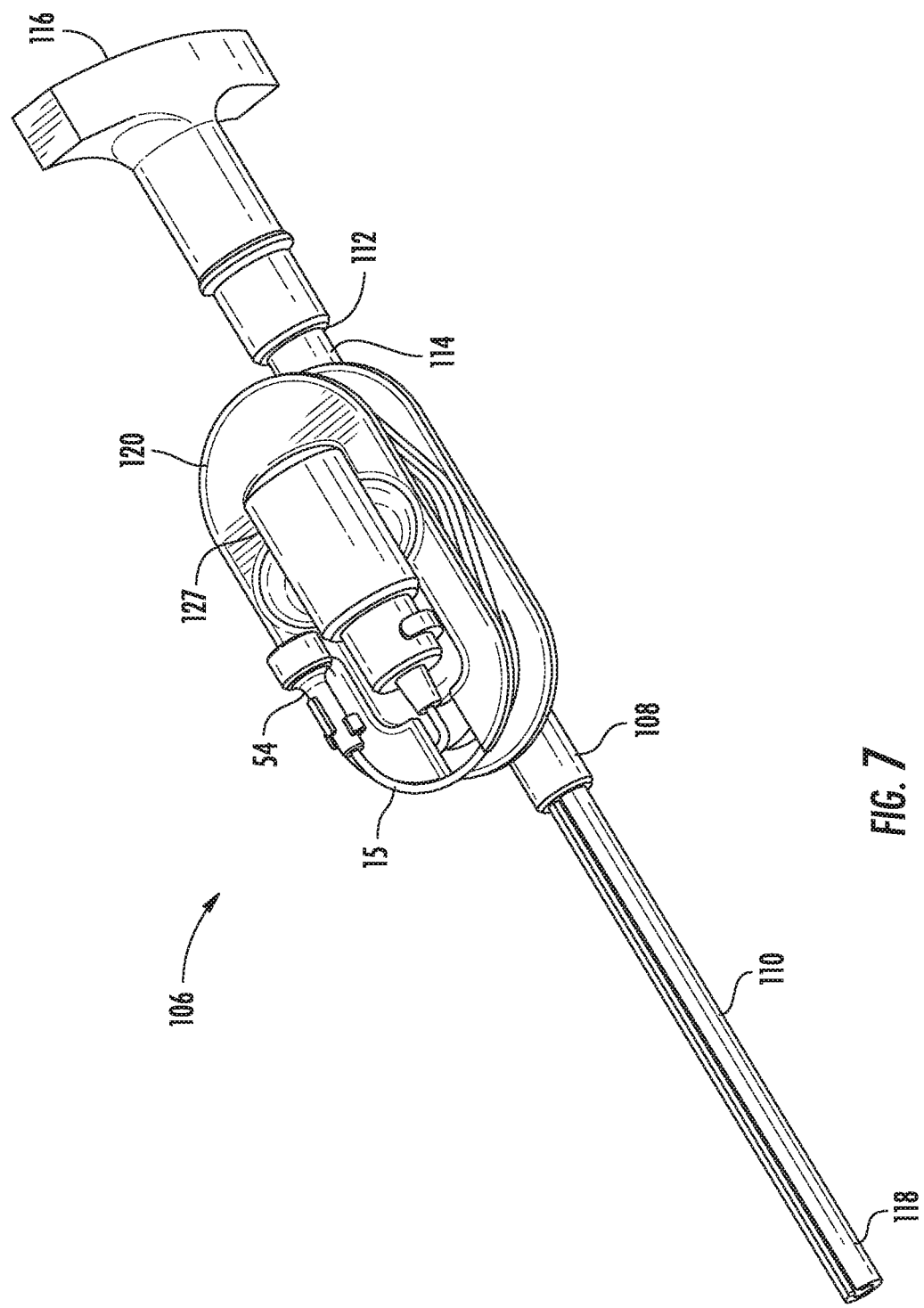
FIG. 7 illustrates an alternative embodiment of the anchor delivery tool, referred to generally as a surgical anchor insertion tool with vertical spool.
Figure 8:
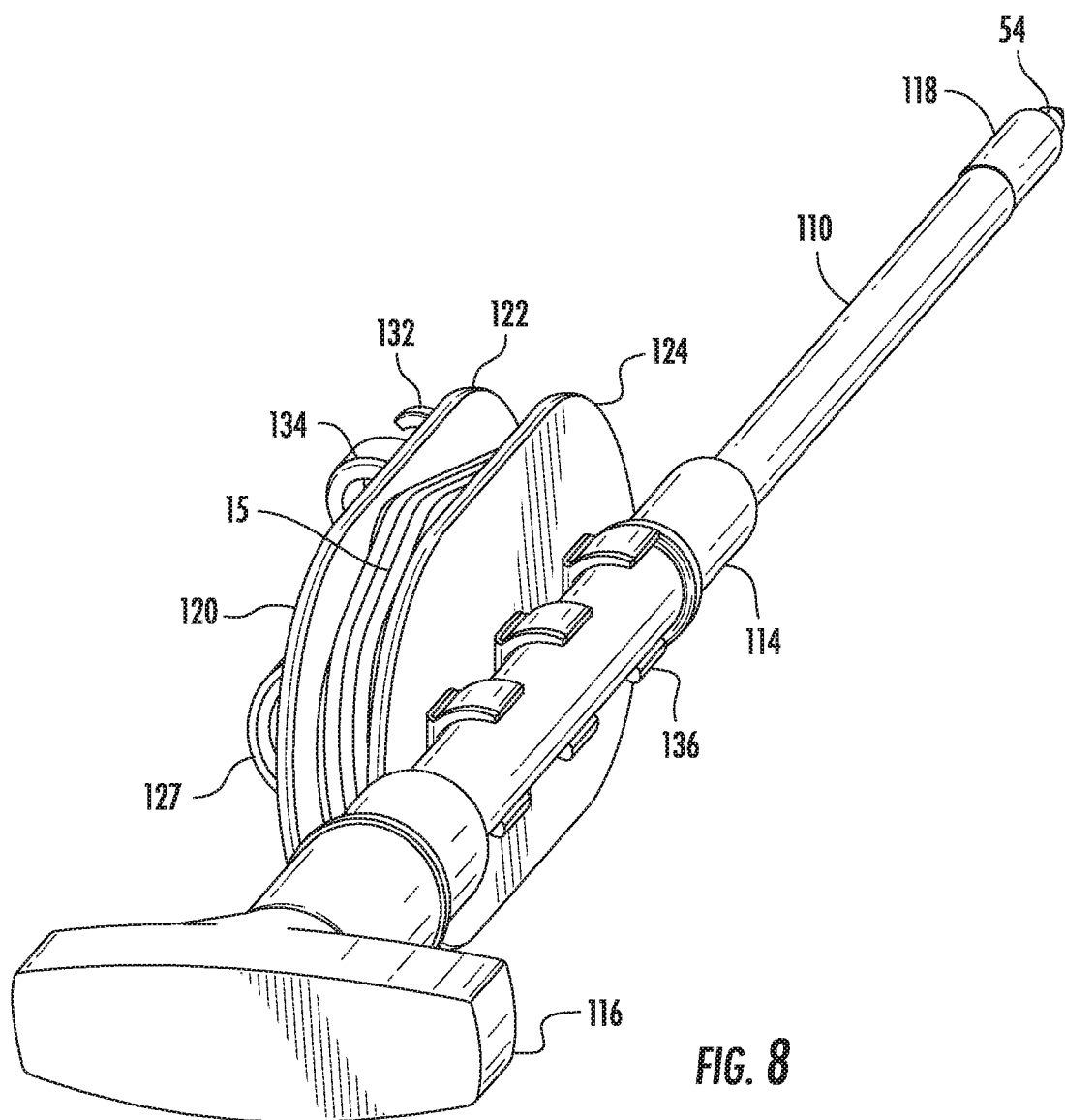
FIG. 8 illustrates the surgical anchor insertion tool with vertical spool, shown with the surgical anchor inserted therein.

FIGS. 7 and 8 illustrate an alternative embodiment of the anchor delivery tool, referred to generally as a surgical anchor insertion tool with vertical spool 106. The surgical anchor insertion tool with vertical spool 106 has a similar construction as described above for the surgical anchor insertion tool 92. The surgical anchor insertion tool with vertical spool 106 comprises a first end 108 configured to engage with a secondary shaft 110, a second end 112, and a main body shaft 114. A handle 116, shown as a T-shaped handle, is attached to or integrally formed to the second end 112. The secondary shaft 110 is configured to include, as a free standing, connectable component, or integrally formed thereto, a surgical anchor engaging member 118. The surgical anchor engaging member 118 is configured to receive and secure the surgical sensor anchor 12/54/354 thereto. Attached to at least a portion of the main body shaft 114 is a vertical spool 120.

Figure 9:
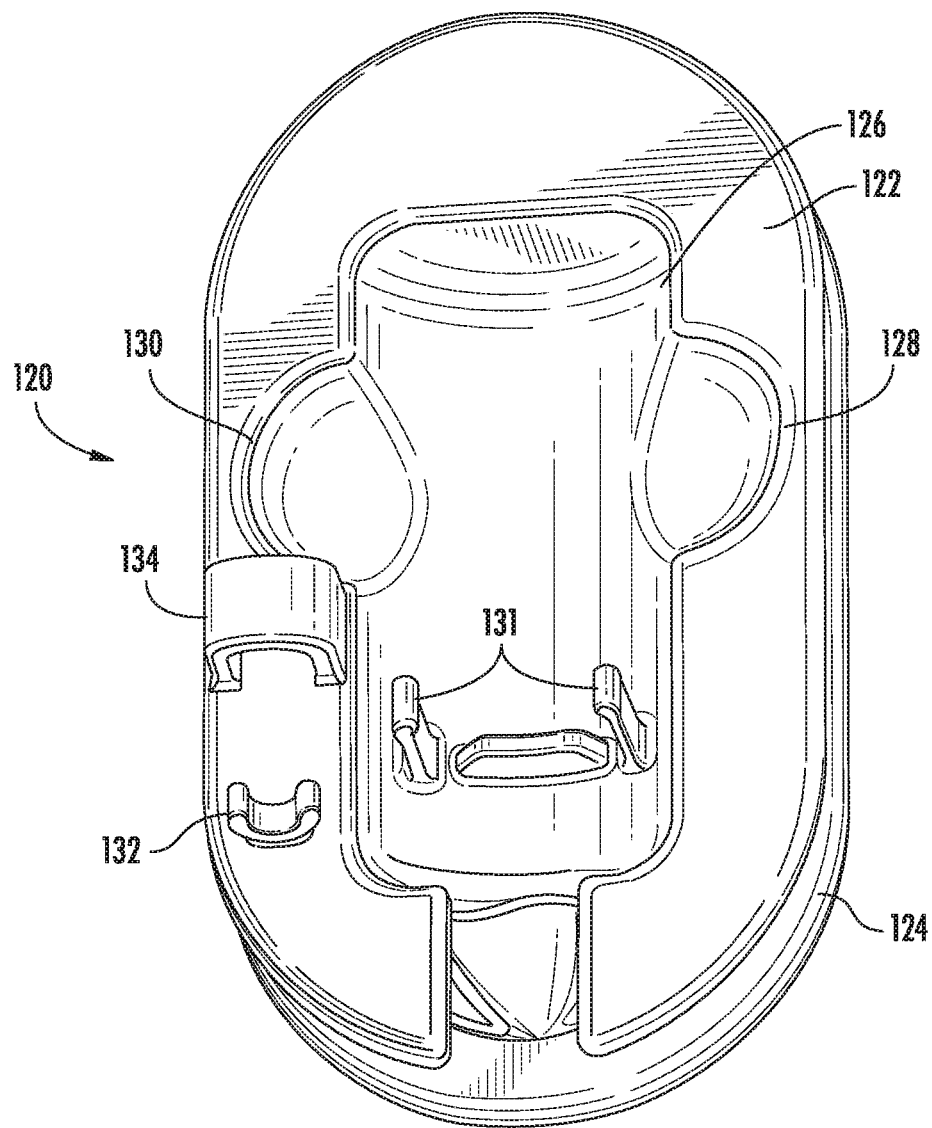
FIG. 9 is a perspective view of an illustrative embodiment of a vertical spool, showing the first flanged member.
Figure 10:
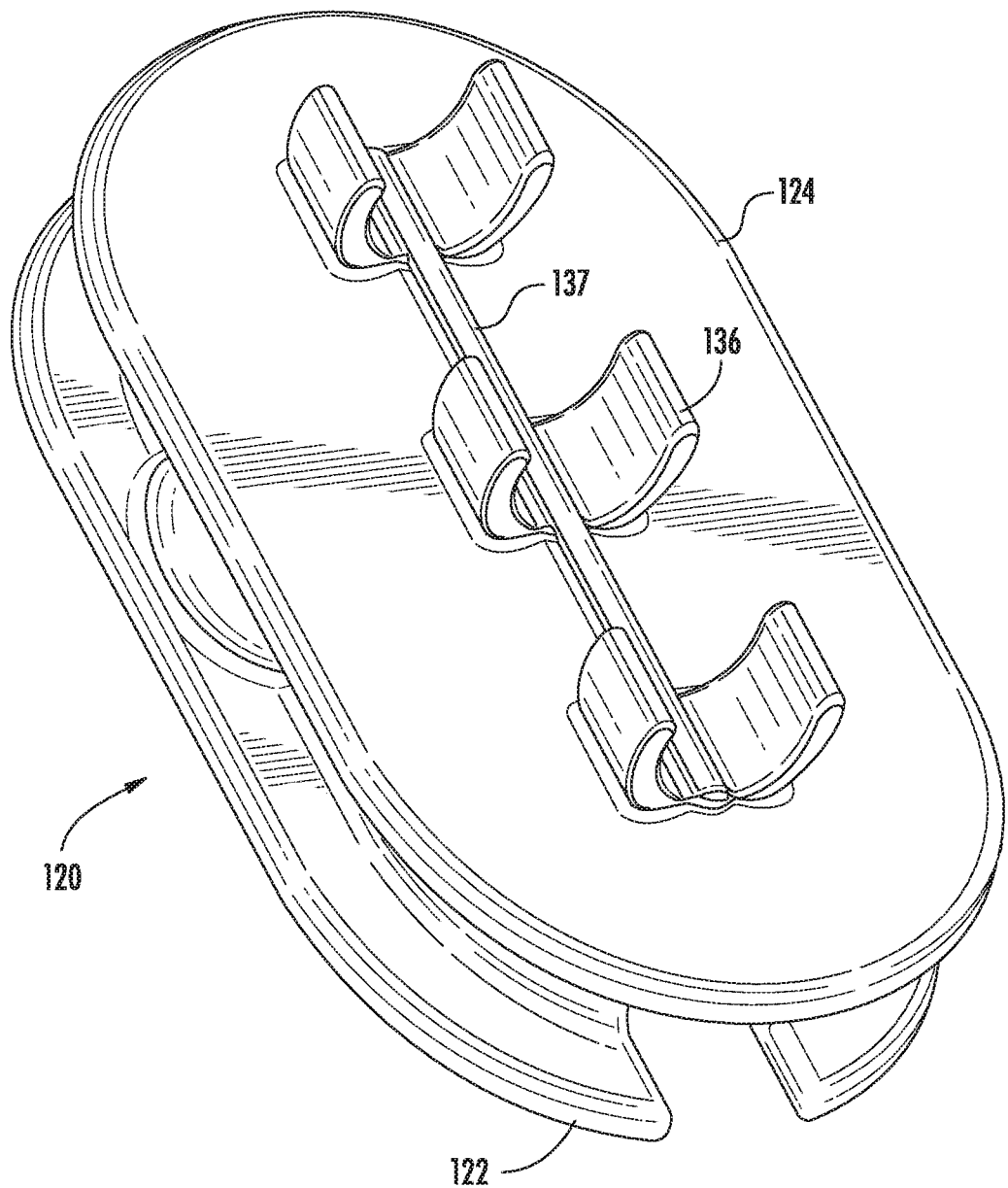
FIG. 10 is a perspective view of the vertical spool, showing the second flanged member.

Referring to FIGS. 9 and 10, an illustrative example of the vertical spool 120 is shown. The vertical spool 120 comprises two flanged members 122 and 124 separated by a hub (not shown); the hub being a sufficient size to allow the electrical wires of the sensor to be wrapped or unwrapped. The spool flanged member 122 comprises a first indented or recessed portion 126 sized and shaped to store a sensor connector 127 (FIG. 11) therein. Sensor connector clasp prongs 131 maintain the connector in place when secured thereto. The spool flanged member 122 may also include side recessed portions, 128 and 130. The side recessed portions 128 and 130 allow a user's finger(s) to easily grasp the sensor connector 127, thereby providing a mechanism for easy removal.

The surgical sensor anchor 54 can be secured to the flanged member 122 through sensor clasp cradle prongs 132. A hood cover 134 covers the sharp end of the surgical sensor anchor 54. The spool flanged member 124 may contain a plurality of main body cradle prongs 136, see FIG. 10, each sized and shaped to allow portions of the main body shaft 114 to secure thereto. A vertical rib 137 may be used, and placed within the sensor clasp cradle prongs 132, to prevent the vertical spool 120 from spinning.

Figure 11:
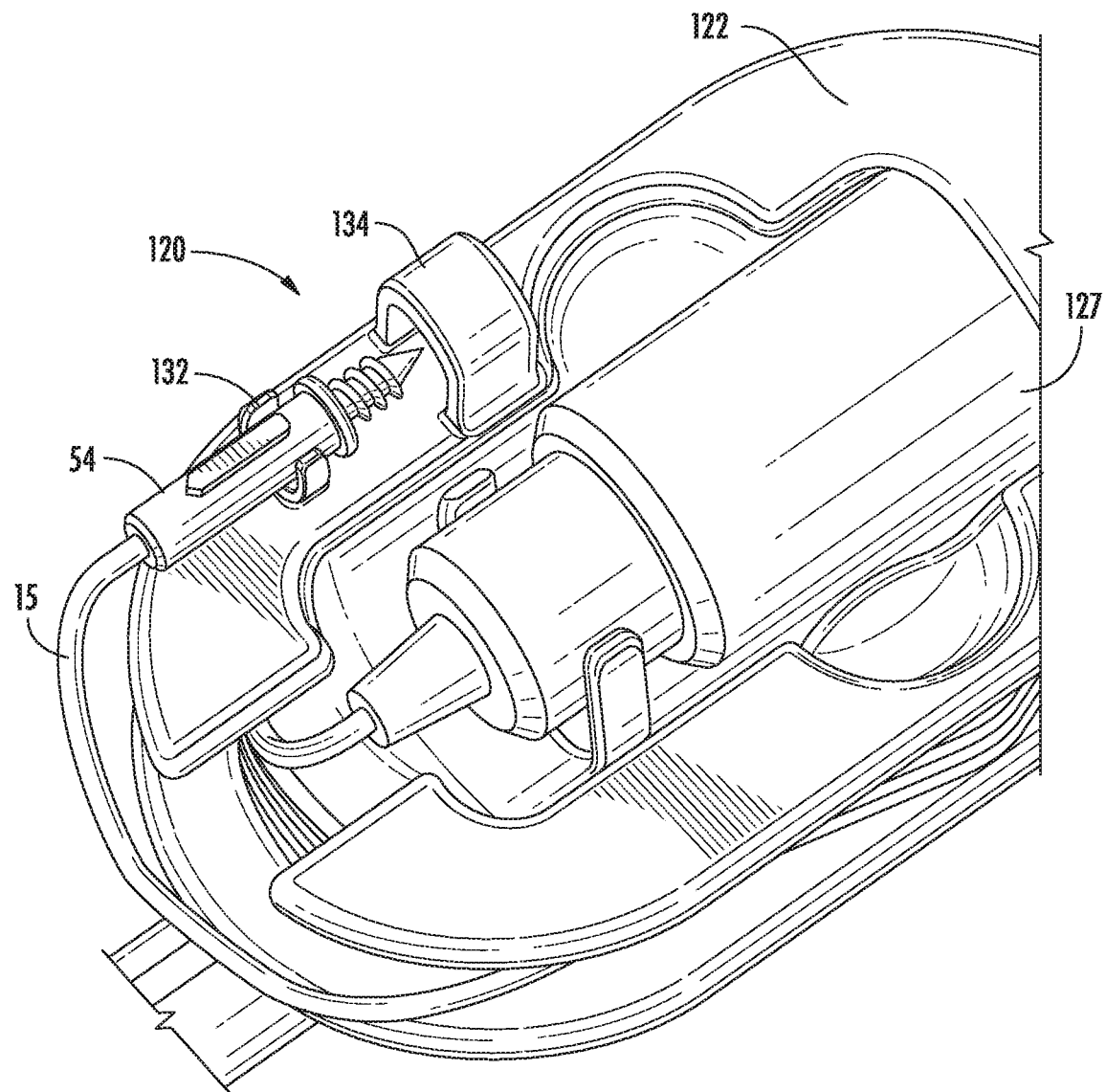
FIG. 11 is a close-up view of the vertical spool.
Figure 12:
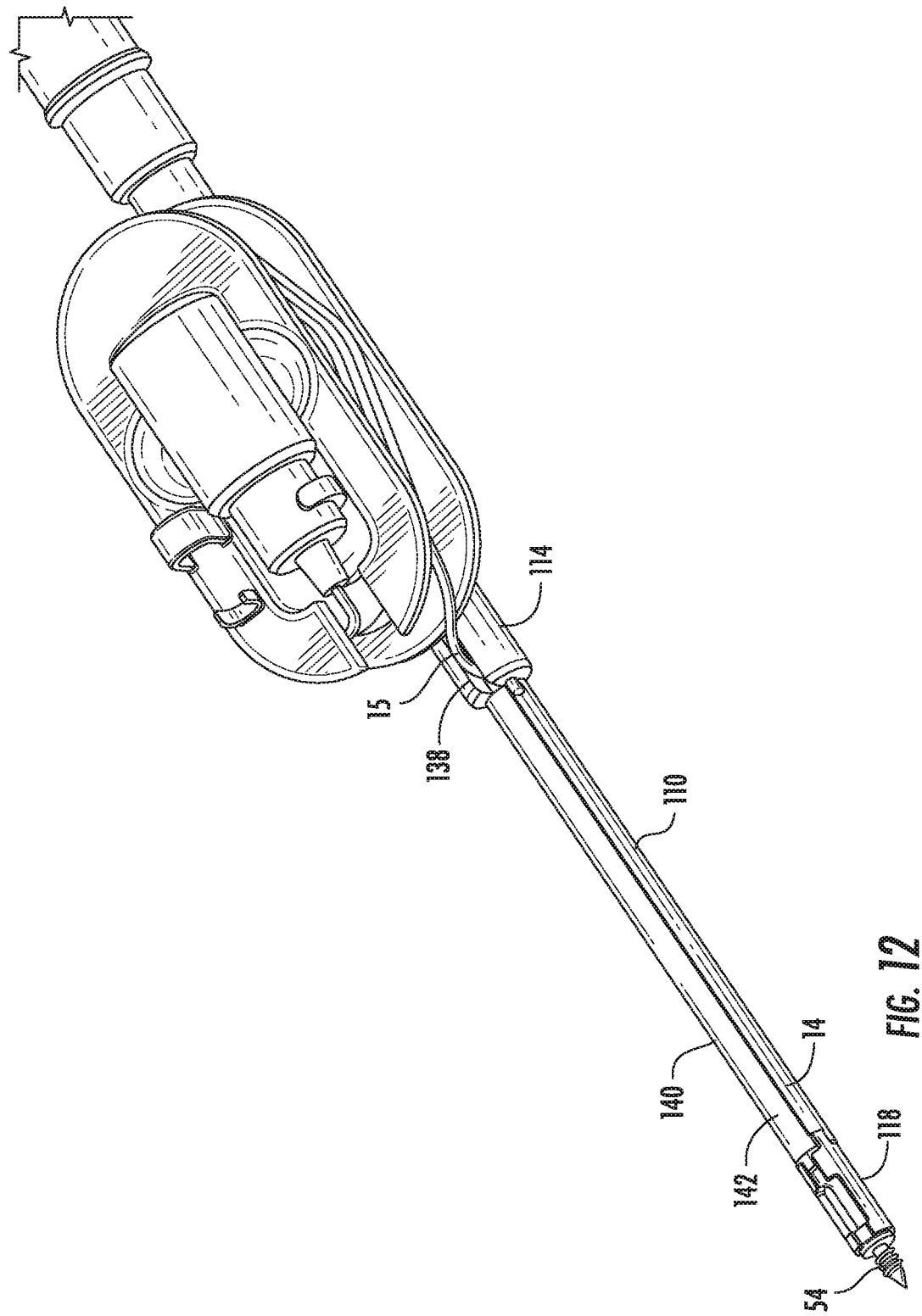
FIG. 12 is a partial view of the surgical anchor insertion tool with vertical spool.
Figure 13:
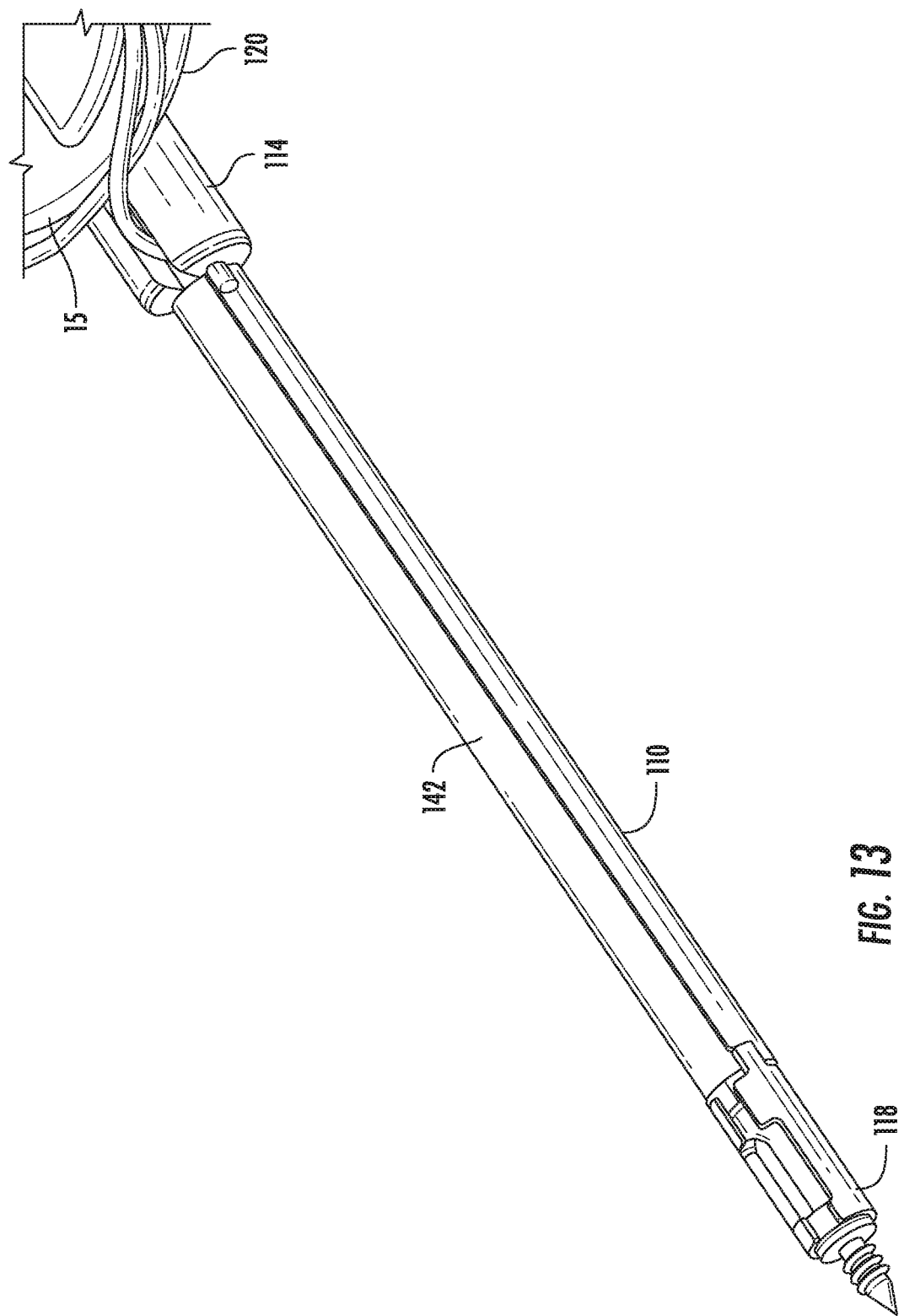
FIG. 13 is an alternative partial view of the surgical anchor insertion tool with vertical spool.

Referring to FIG. 11, the vertical spool 120 is shown with the surgical sensor anchor 54 slid out of the hood cover 134. The user can remove the surgical sensor anchor 54 by snapping it out of sensor clasp cradle prongs 132. The user can then uncoil enough of the wire 15 to insert the surgical sensor anchor 54 into the distal end of the surgical anchor insertion tool with vertical spool 106, i.e. the surgical anchor engaging member 118. As illustrated in FIG. 12, the main body shaft 114 and the secondary shaft 110 comprise a body having a slotted opening 138 for main body shaft 114, and a slotted opening 140 for the secondary shaft 110. The slotted openings 138 and 140 are sized and shaped to receive and store therein the sensor electrical wire 15. A wire retainer, illustrated herein as a rotatable sheath 142, can be rotated to secure the wire therein, see FIG. 13.

Figure 14:
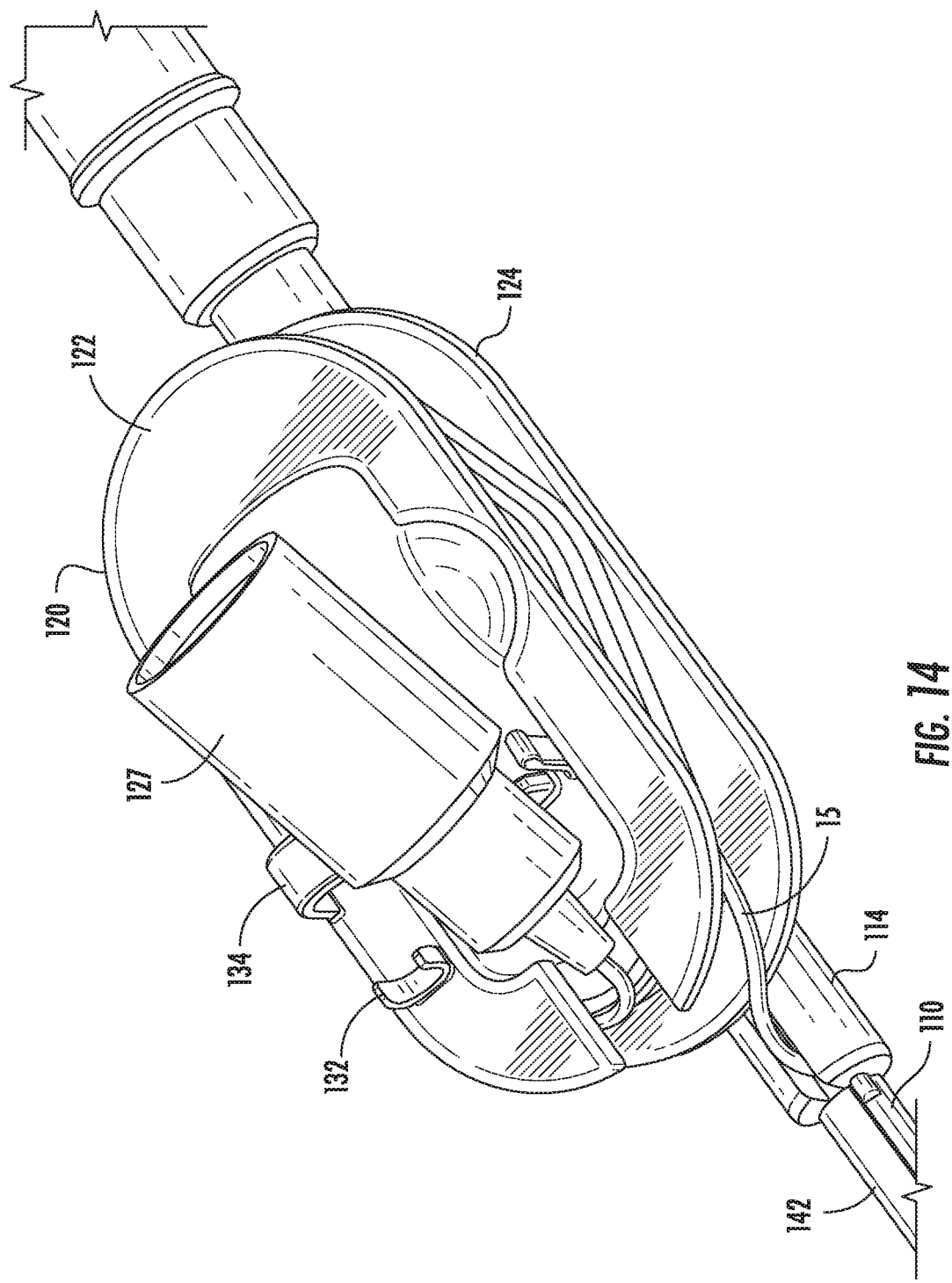
FIG. 14 is a partial view of the surgical anchor insertion tool with vertical spool, shown with the sensor connector partially removed.
Figure 15:
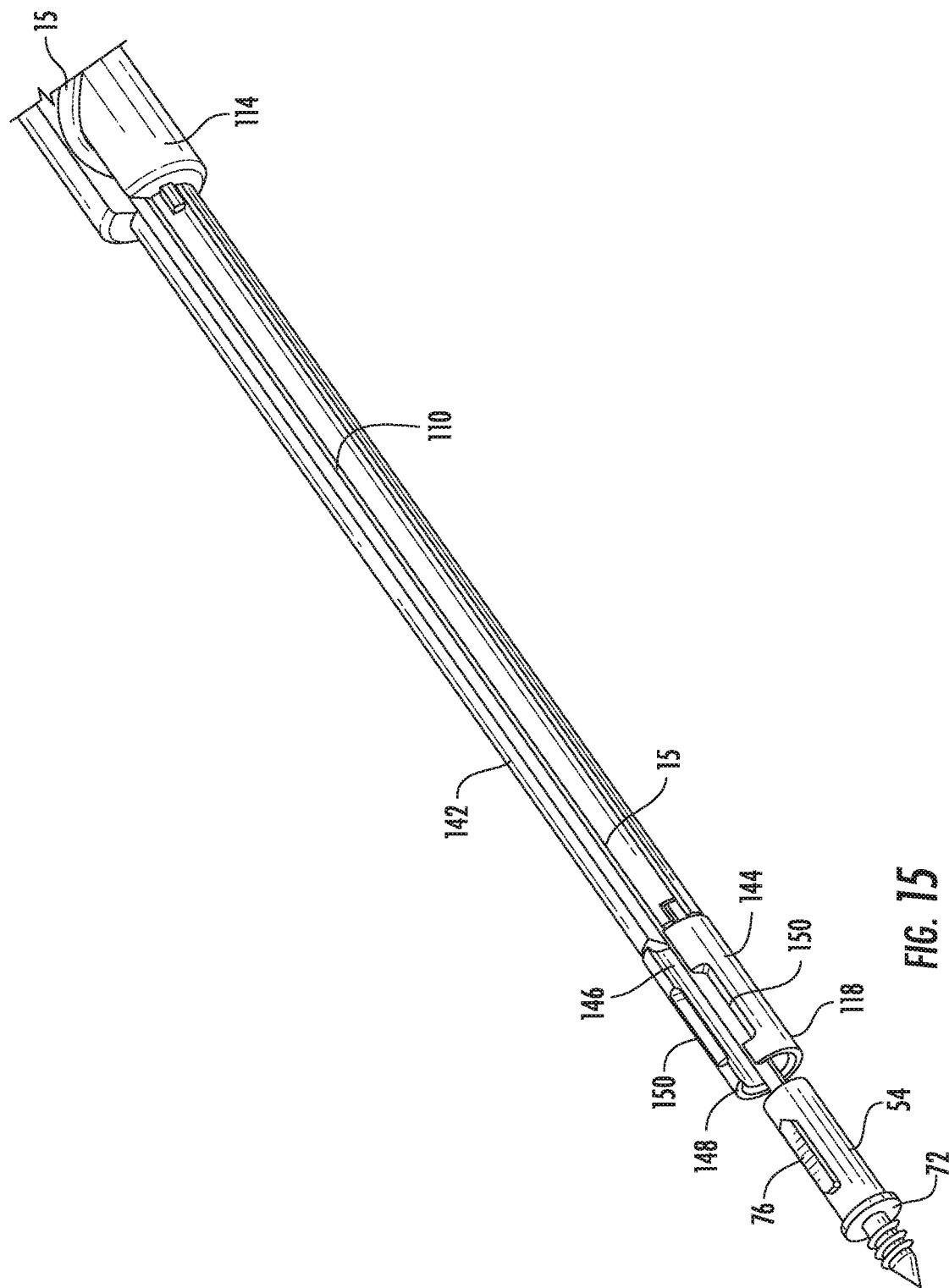
FIG. 15 is an alternative partial view of the surgical anchor insertion tool with vertical spool, shown with the surgical sensor anchor removed.
Figure 16:
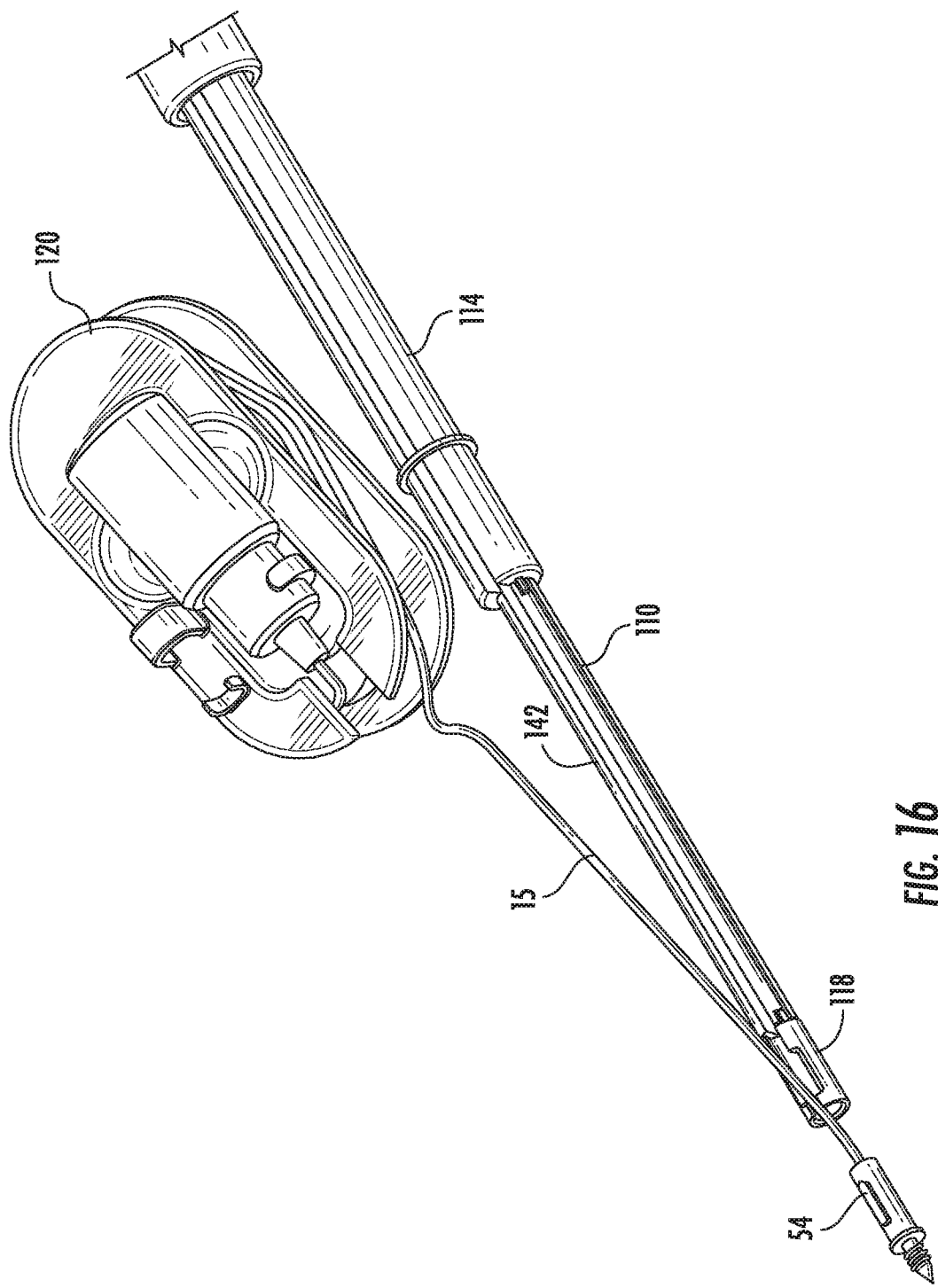
FIG. 16 is an alternative partial view of the surgical anchor insertion tool with vertical spool, shown with the surgical sensor anchor removed.

Once the surgical sensor anchor 54 is secured to the target site, i.e. a desired body portion that requires a surgical procedure, the user can snap the sensor connector 127 out of the spool 120, see FIG. 14, and uncoil the remainder of the sensor electrical wire 15. The wire retainer rotatable sheath 142 is released, see FIG. 15, and with a slight counterclockwise motion, the surgical anchor insertion tool with vertical spool 106 is released from the surgical sensor anchor 54. The surgical anchor insertion tool with vertical spool 106 may then be removed from the surgical site. If needed, the sensor electrical wire 15 and the sensor connector 127 can be left on the vertical spool 120 and detached from the surgical anchor insertion tool with vertical spool 106 if the surgical sensor anchor 54 is not connected to sensor equipment, see FIG. 16.

Referring back to FIG. 15, the surgical sensor anchor 54 is removed from the surgical anchor insertion tool with vertical spool 106, thereby exposing the surgical anchor engaging member 118. The surgical anchor engaging member 118 includes a generally cylindrical body 144 having a longitudinal slot 146 running the length of the cylindrical body 144 and terminating in an opening 148. A portion of the longitudinal slot 146 contains cut-outs 150 which are sized and shaped to receive the insertion tool engaging member 76 of the surgical sensor anchor 54. The opening 148 is sized and shaped to be larger than the diameter of the surgical sensor anchor 54. To rest securely in the surgical anchor engaging member 118, the surgical sensor circumferential flange 72 is sized to have a larger diameter than the diameter of the opening 148 so as not to be fully inserted therein.

Figure 17:
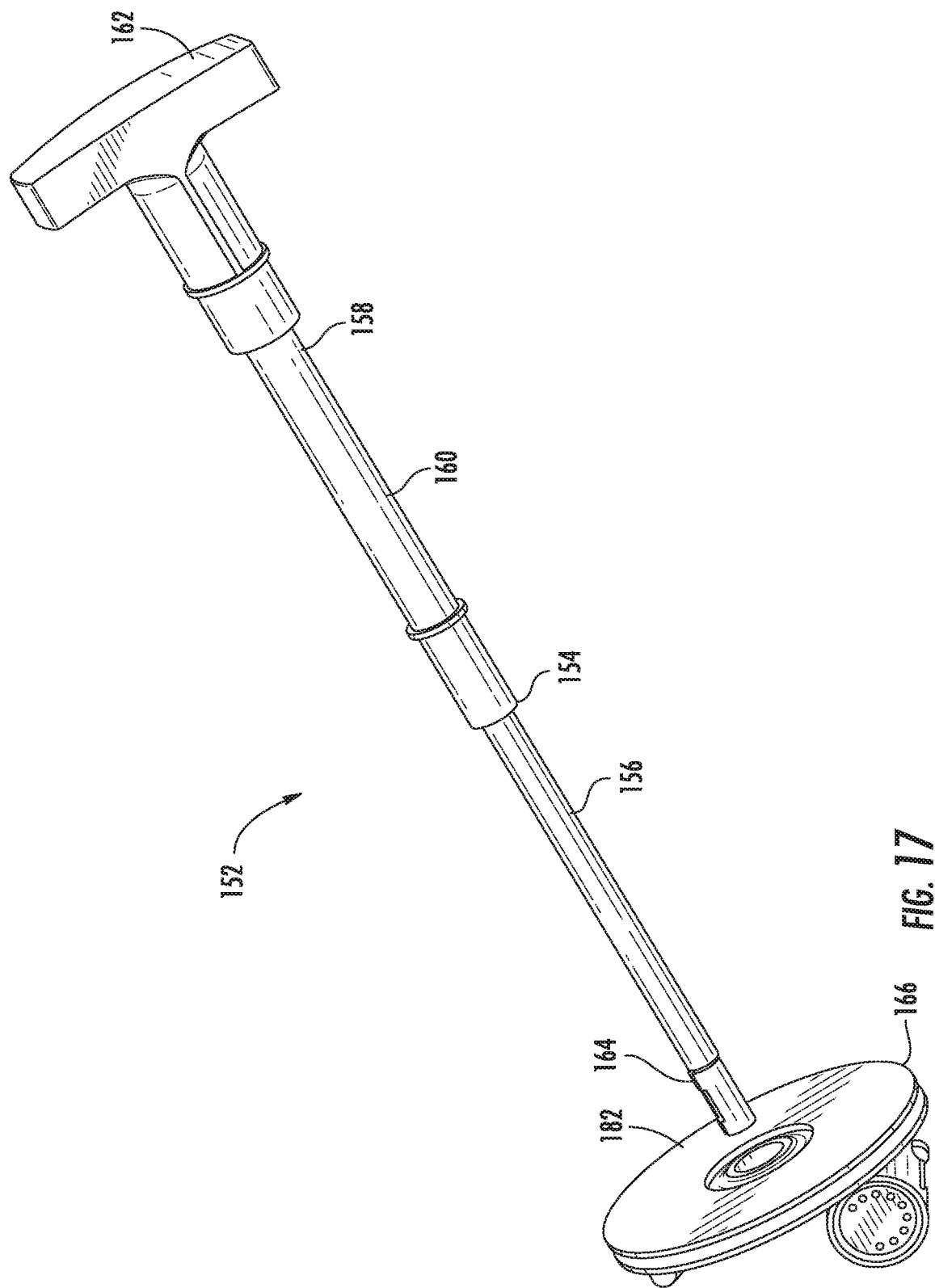
FIG. 17 is a perspective view of an alternative embodiment of the anchor delivery tool, referred to generally as a surgical anchor insertion tool with a horizontal spool.
Figure 18:
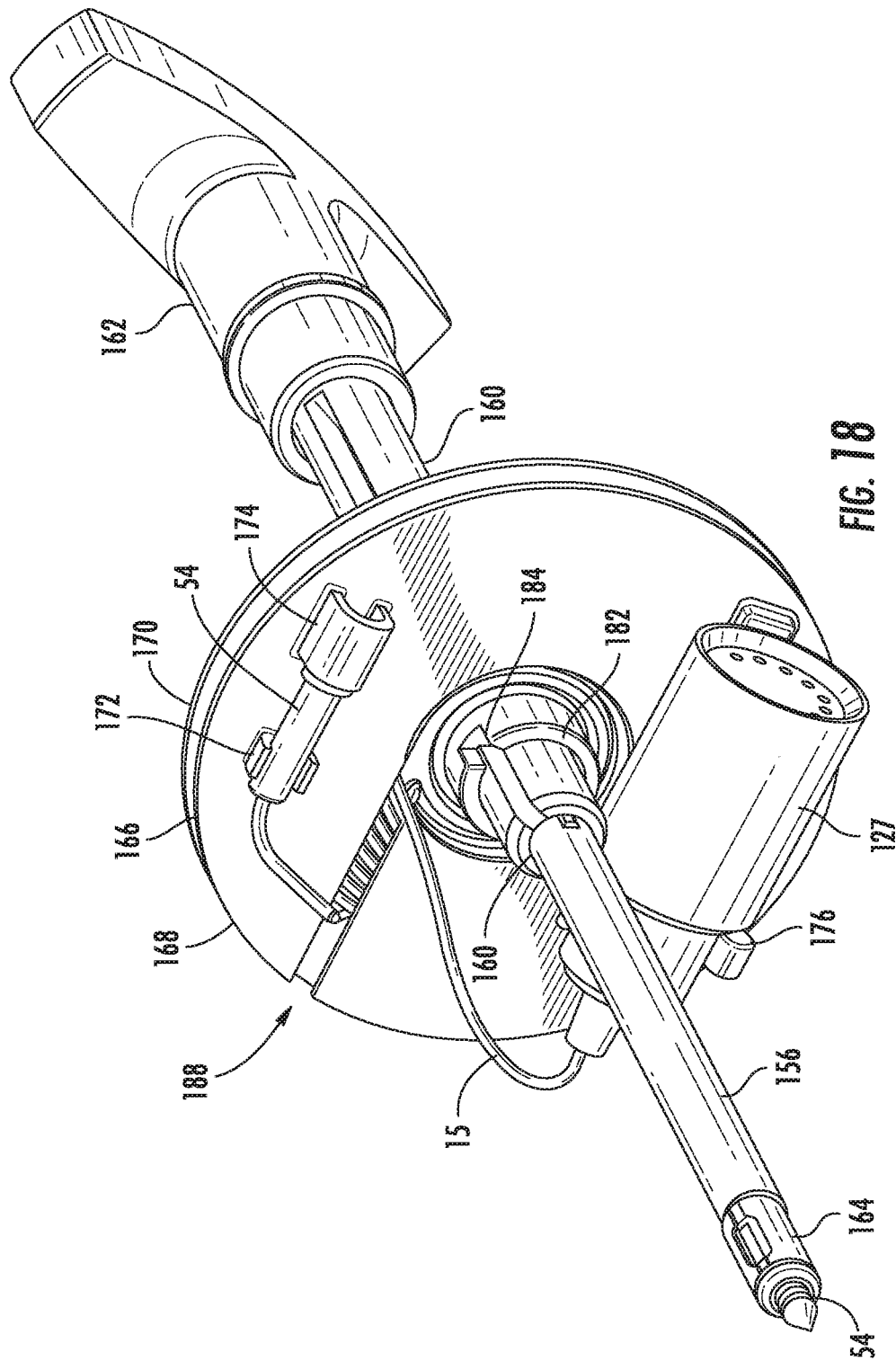
FIG. 18 is an alternative perspective view of the surgical anchor insertion tool with horizontal spool.
Figure 19:
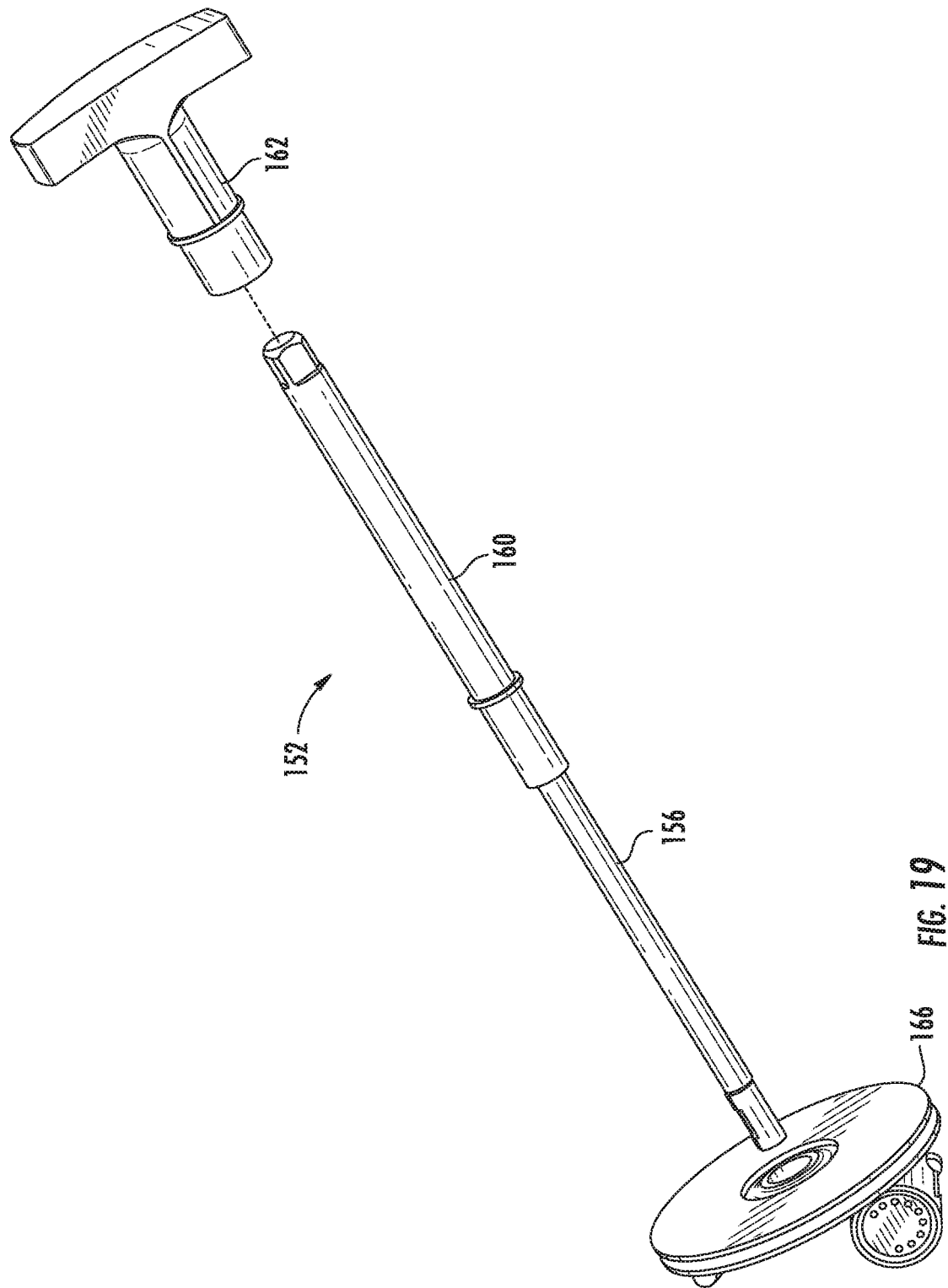
FIG. 19 is an exploded view of the surgical anchor insertion tool with horizontal spool.

Referring to FIGS. 17-19, an alternative embodiment of the anchor delivery tool, referred to generally as a surgical anchor insertion tool with horizontal spool 152 is illustrated. The surgical anchor insertion tool with horizontal spool 152 has a similar construction as described above for the surgical anchor insertion tool 92 or 106. The surgical anchor insertion tool with horizontal spool 152 comprises a first end 154 configured to engage with a secondary shaft 156, a second end 158, and a main body shaft 160. A handle 162, shown as a T-shaped handle, is attached to or integrally formed to the second end 158. The secondary shaft 156 is configured to include, as a free standing, connectable component, or integrally formed thereto, a surgical anchor engaging member 164. The surgical anchor engaging member 164 is configured to receive and secure the surgical sensor anchor 12/54/354 thereto. Each of the components described above comprise the same features and construction as that describe for the surgical anchor insertion tool with vertical spool 106.

Attached to at least a portion of the main body shaft 160 is a horizontal spool 166. The horizontal spool 166 comprises a first flanged member 168, a second flanged member 170, and a hub (not shown, but preferably in the shape of a spool drum) separating the two flanged members. The hub is of a sufficient size to allow the electrical wires of the sensor to be wrapped or unwrapped. The horizontal spool first flanged member 168 may be configured to store one or more components, such as the surgical sensor anchor 54 or the surgical sensor connector 127. Accordingly, the horizontal spool first flanged member 168 may comprise a sensor anchor cradle with prongs 172 configured to maintain the surgical sensor anchor 54 in place, when secured thereto, and a hood 174. The horizontal spool first flanged member 168 may further comprise a sensor connector cradle with prongs 176 configured to maintain the sensor connector 127 in place when secured thereto.

Figure 20:
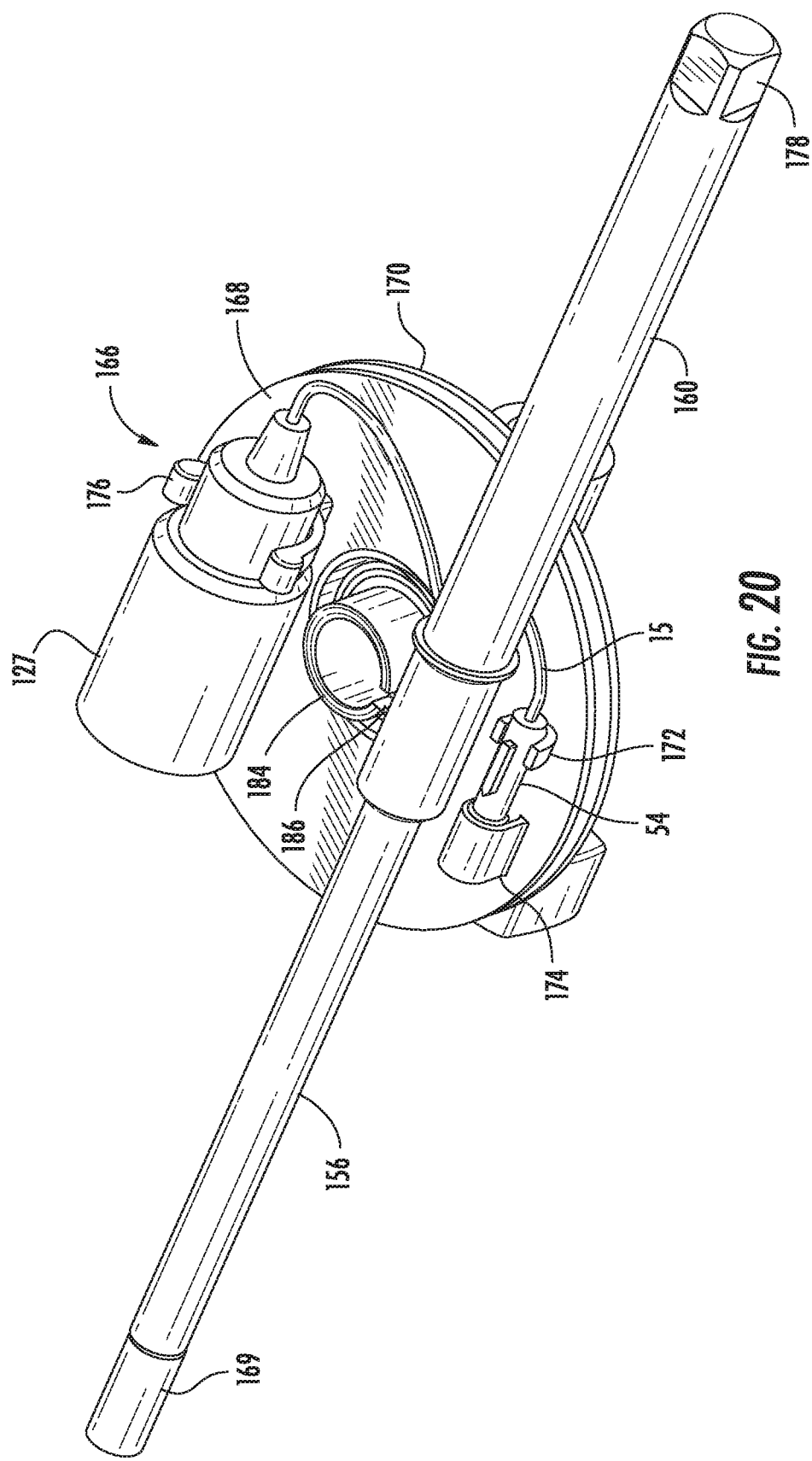
FIG. 20 is a perspective view of a first side of the horizontal spool.
Figure 21:
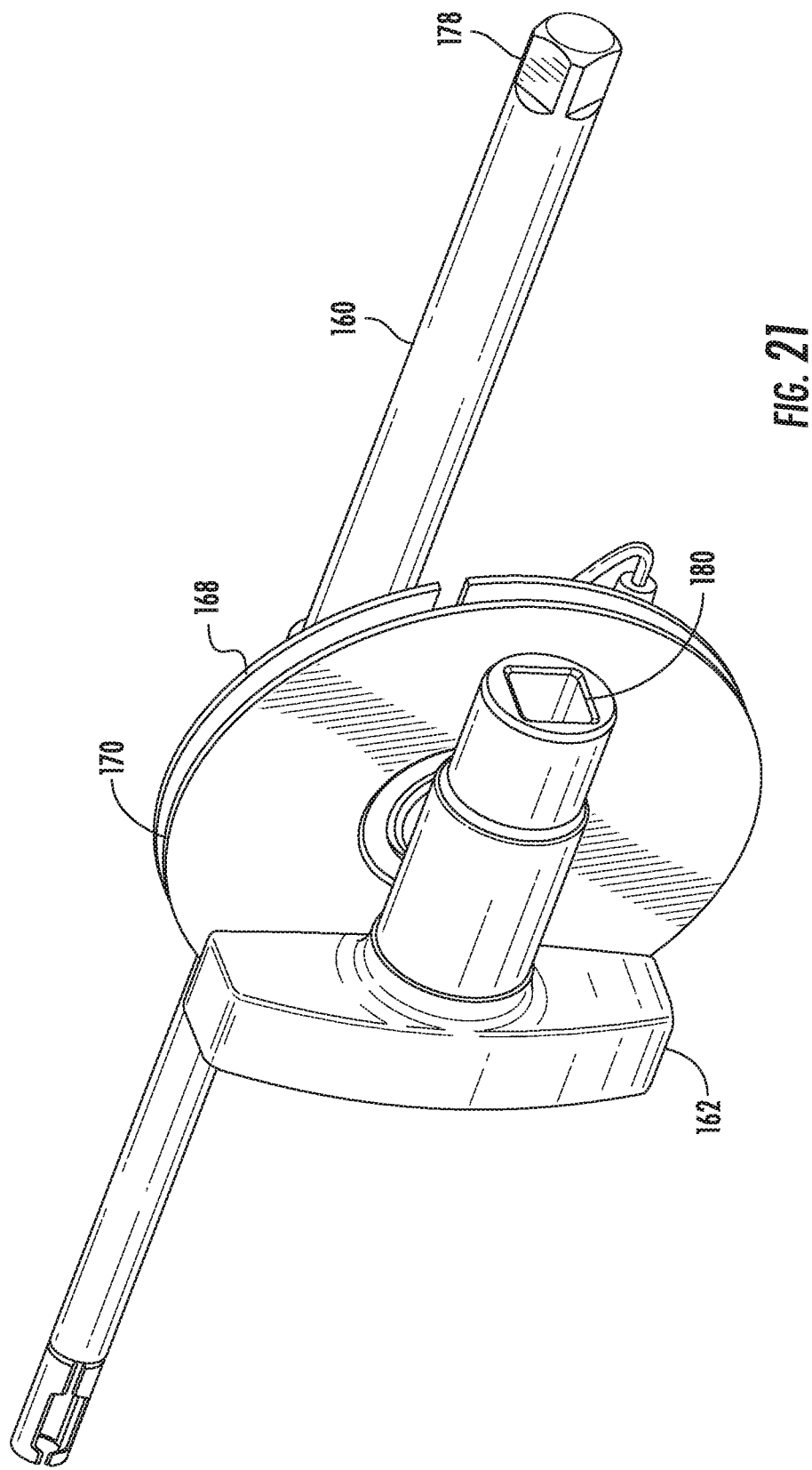
FIG. 21 is a perspective view of a second side of the horizontal spool.

FIG. 20 illustrates the horizontal spool 166 configured for transporting of one or more components. In this configuration, the surgical sensor 14 is mounted into the surgical sensor anchor 54. The surgical sensor anchor 54 is snapped into the sensor cradle with prongs 172 on the spool for transport. The hood 174 covers the sharp tip of the surgical sensor anchor 54. The sensor wire 15 is coiled onto the spool 166, and then the connector 127 is snapped into its cradle 176. The anchor delivery tool and T-shaped handle may or may not be included with the kit. As illustrated, the secondary shaft 156, main body shaft 160, and the surgical anchor engaging member 164 are shown secured to the horizontal spool 166. The T-shaped handle 162 is shown secured to the second flanged 170 member, see FIG. 21. As illustrated, the main body 160 has a hex-shaped end 178 sized and shaped to secure to the corresponding T-shaped handle hex-shaped coupler 180.

The horizontal spool 166 comprises a central opening 182, see for example FIG. 17. The central opening 182 has a sufficient diameter to allow portions of the surgical anchor insertion tool 152 to pass therethrough. Accordingly, a user can separate the main body 160 and T-shaped handle 162, see FIG. 19, from the horizontal spool 166, if necessary, and insert the main body 160 into the central opening 182 with the tool delivery components attached thereto, facing away from the distal end (the end furthest away from a user when the user is engaging the T-shaped handle). A central support member 184, having a generally cylindrical shape with a slotted cut out 186, supports portions of the main body 160 when inserted therein, see FIG. 18 and FIG. 20. The slotted cut out 186 is sized and shaped so as to align with the slotted opening 140 of secondary shaft 110 of the main body 160. To aid in dispensing or storing of the sensor electrical wire 15, the horizontal spool first flanged member 168 also contains a cut out channel 188.

Figure 22:
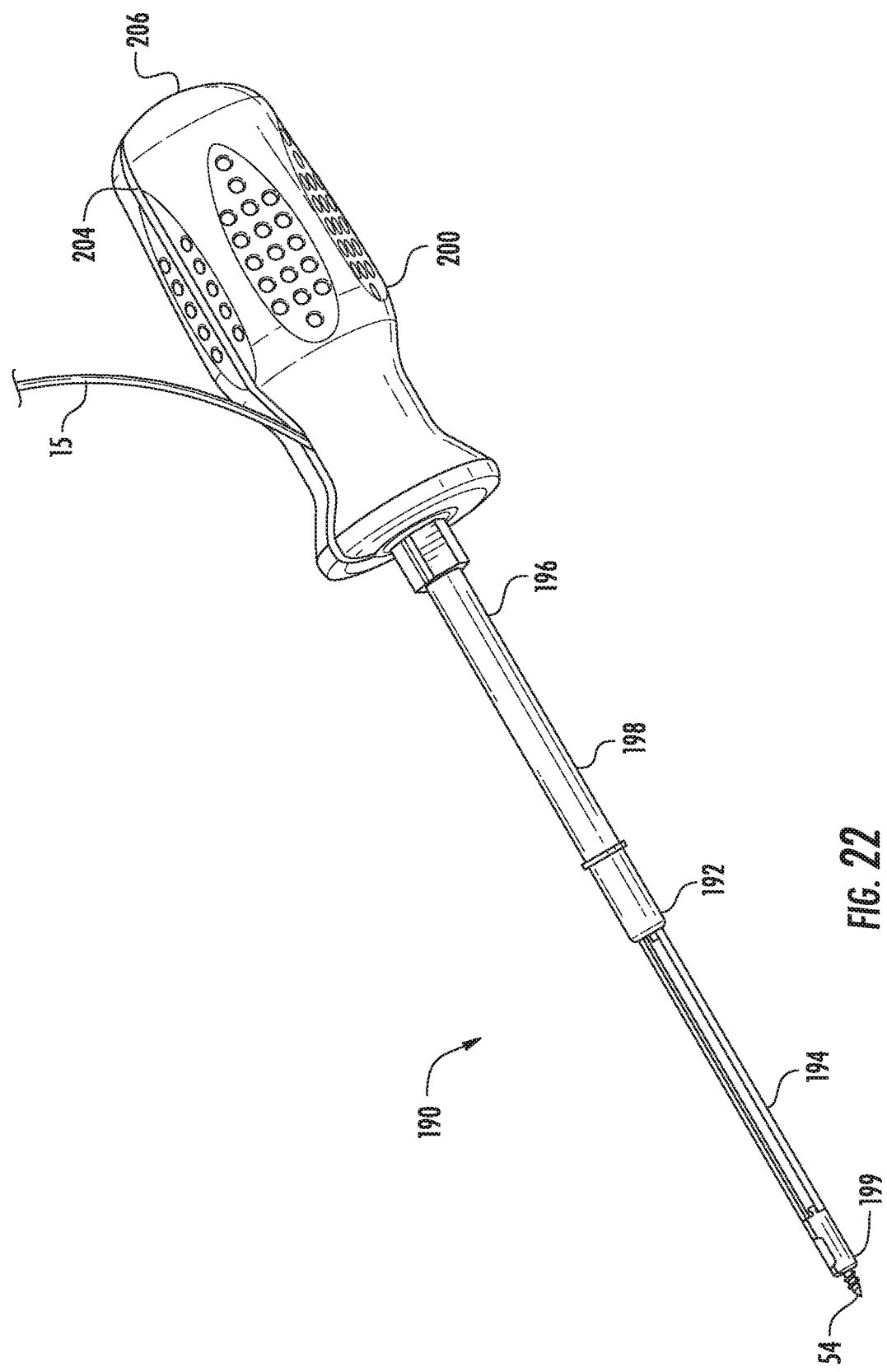
FIG. 22 is a perspective view of an alternative embodiment of the anchor delivery tool, referred to generally as a pass through surgical anchor insertion tool.
Figure 23:
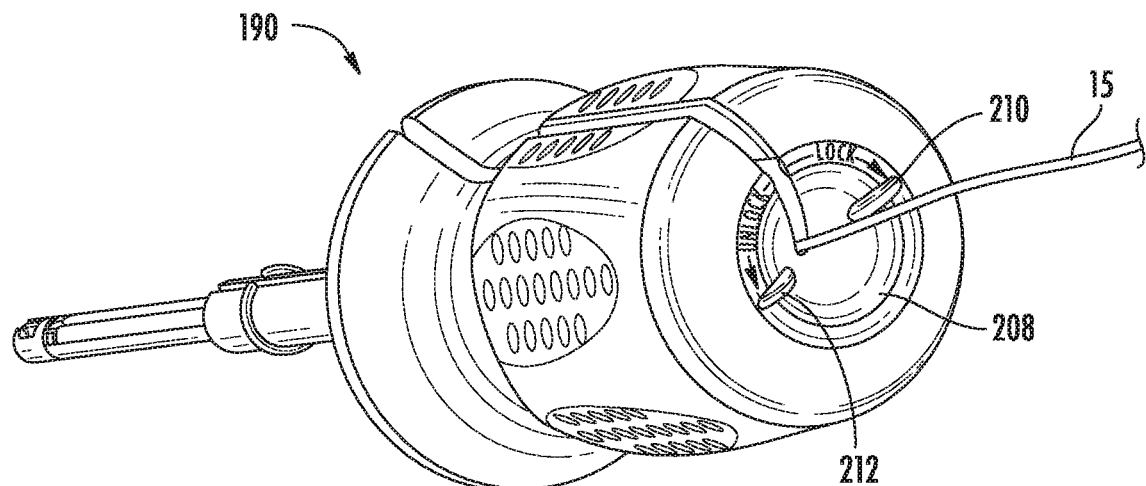
FIG. 23 is a top view of the pass through surgical anchor insertion tool, illustrating the unlocked position.
Figure 24:
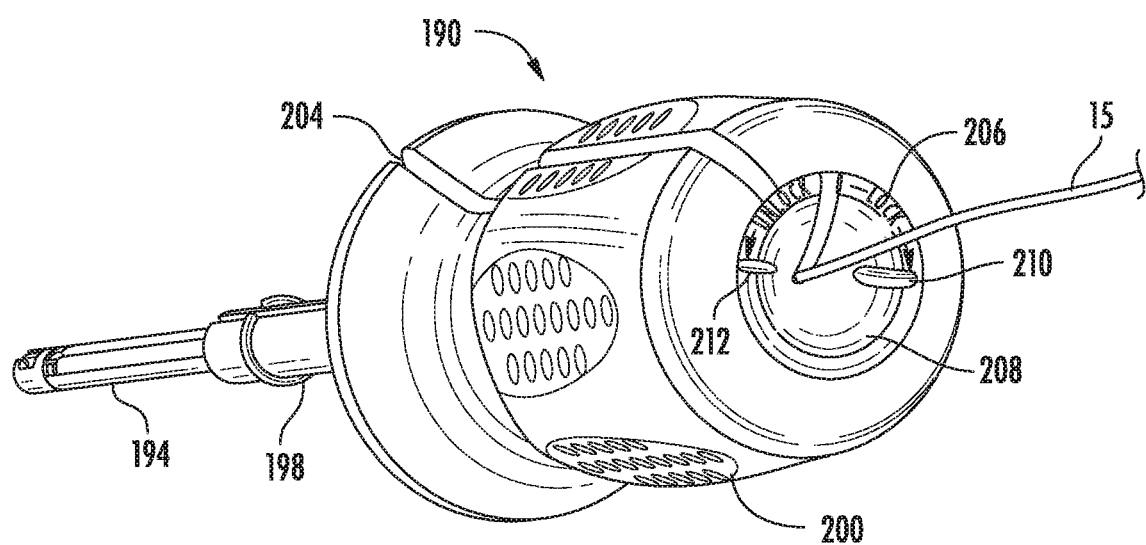
FIG. 24 is a top view of the pass through surgical anchor insertion tool, illustrating the locked position.

Referring to FIGS. 22-24, an alternative embodiment of the anchor delivery tool, referred to generally as a pass through surgical anchor insertion tool 190 is illustrated. The pass through surgical anchor insertion tool 190 has the same construction as described above for the surgical anchor insertion tool 106 or 152, differing in the handle portion. The pass through surgical anchor insertion tool 190 comprises a first end 192 configured to engage with a secondary shaft 194, a second end 196, a main body shaft 198, and a surgical anchor engaging member 199. A handle 200 is attached to or integrally formed to the second end 196. Except for the handle 200, each of the components described above comprise the same features and construction as that described for the surgical anchor insertion tools, 106 or 152.

Figure 25:
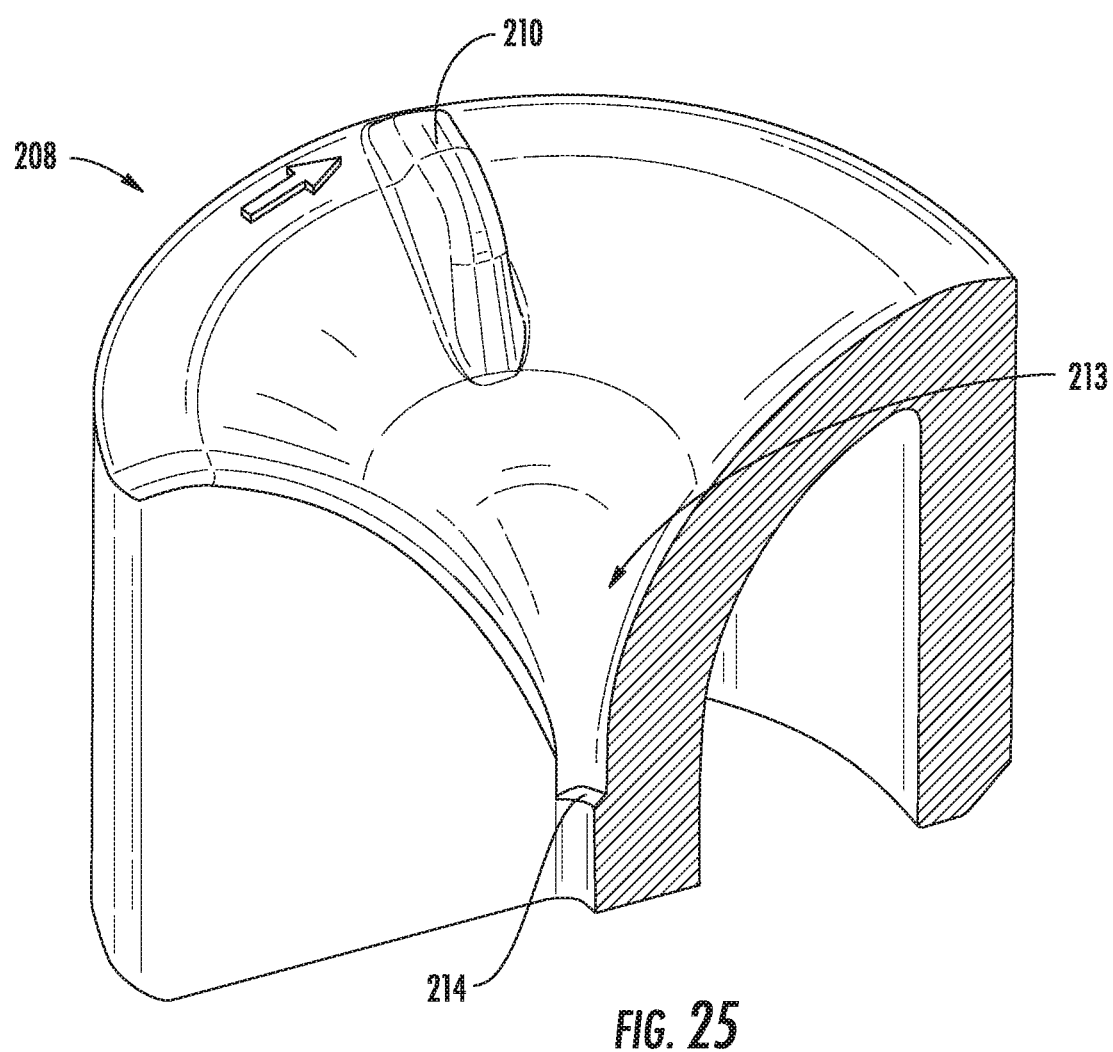
FIG. 25 is a cross sectional view of a wire locking member.
Figure 26:
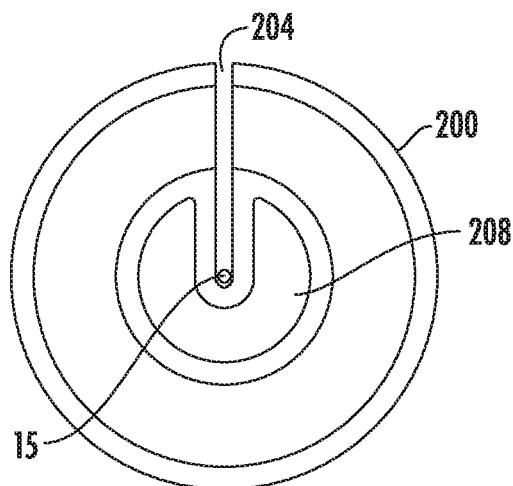
FIG. 26 is a schematic representation of the wire locking member in the unlocked position.
Figure 27:
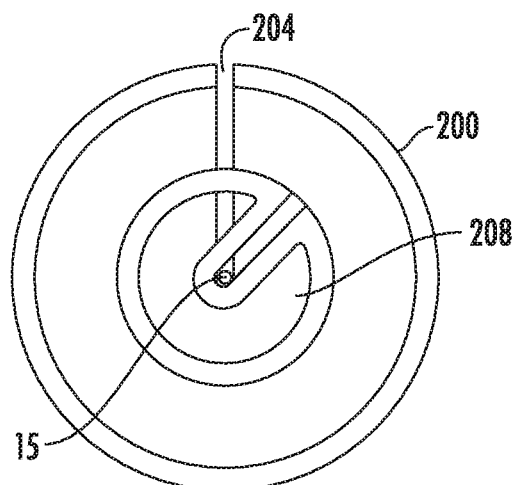
FIG. 27 is a schematic representation of the wire locking member in the locked position.

The handle 200 comprises a handle body 202 having an open slot 204 running the entire length. The open slot 204 is sized and shaped to receive and hold a portion of the sensor electrical wire 15. At the top surface 206 is a handle wire retaining member 208. Rotating the wire retaining member 208 by gripping the tabs 210 and 212 locks the sensor surgical wire 15 in place, see FIGS. 23 and 24. FIG. 25 illustrates a cross sectional view of the handle wire retaining member 208. The handle wire retaining member 208 contains an inwardly sloping funnel surface 213, ending in an offset 214. The offset 214 cams into place to trap the sensor electrical wire 15, see FIGS. 26 and 27.

Figure 28:
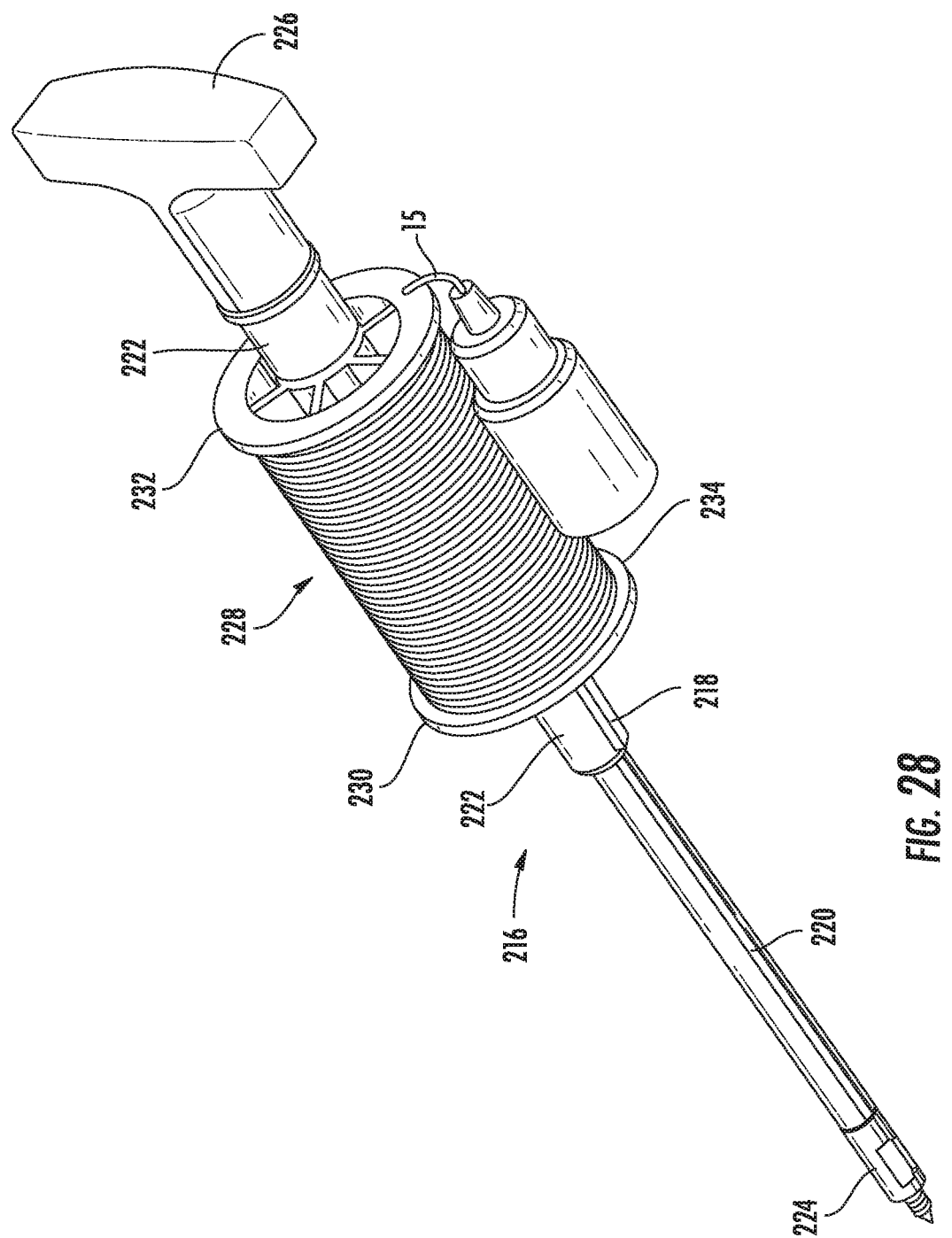
FIG. 28 is a perspective view of an alternative embodiment of the anchor delivery tool, referred to generally as a surgical anchor insertion tool with spool.

Referring to FIG. 28, an alternative embodiment of the anchor delivery tool, referred to generally as a surgical anchor insertion tool with spool 216 is illustrated. The surgical anchor insertion tool with spool 216 comprises the same features as any of the other delivery tools described herein, differing in the spool connection, and having a first end 218 configured to engage with a secondary shaft 220, a main body shaft 222, a surgical anchor engaging member 224, and a handle 226. The spool 228 comprises a first flanged member 230, a second flanged member 232, and a drum 234 (shown with electrical wire 15 wrapped around). The spool 228 preferably secures to portions of the main body shaft 222.

Figure 29:
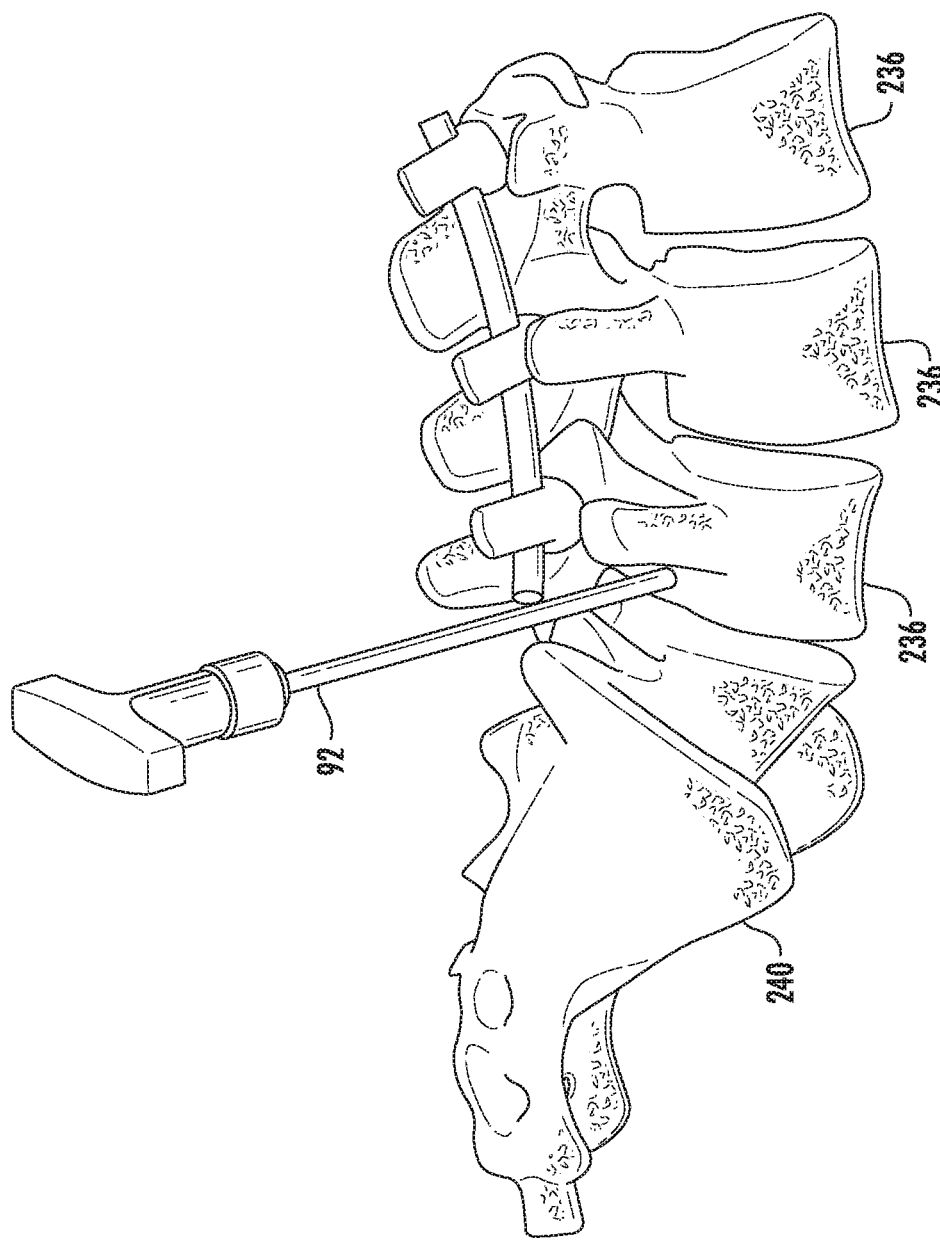
FIG. 29 illustrates the use of the surgical anchor insertion tool to deliver the surgical anchor to one or more vertebral bodies of the spinal cord.
Figure 30:
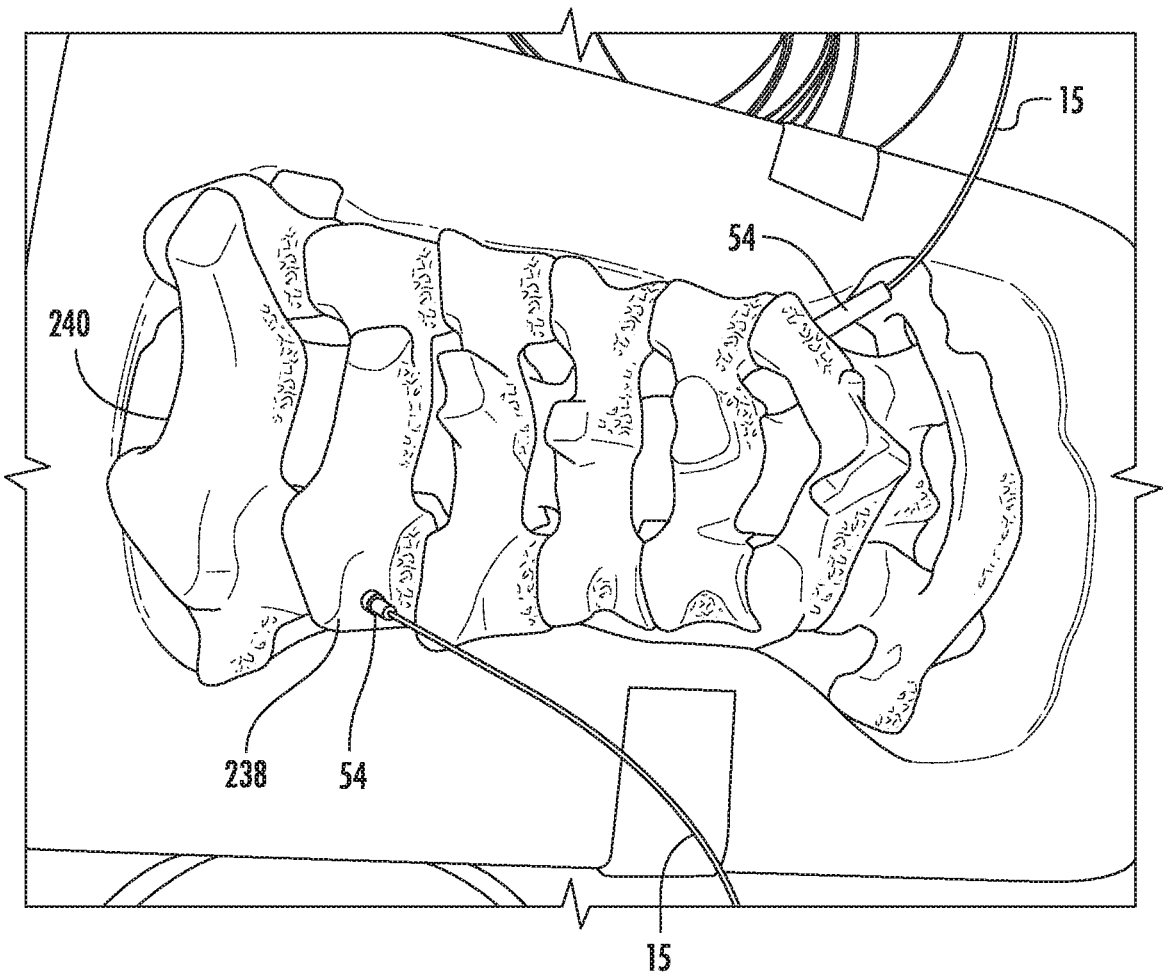
FIG. 30 illustrates the insertion of multiple surgical anchors attached to multiple, independent vertebral bodies.
Figure 31:
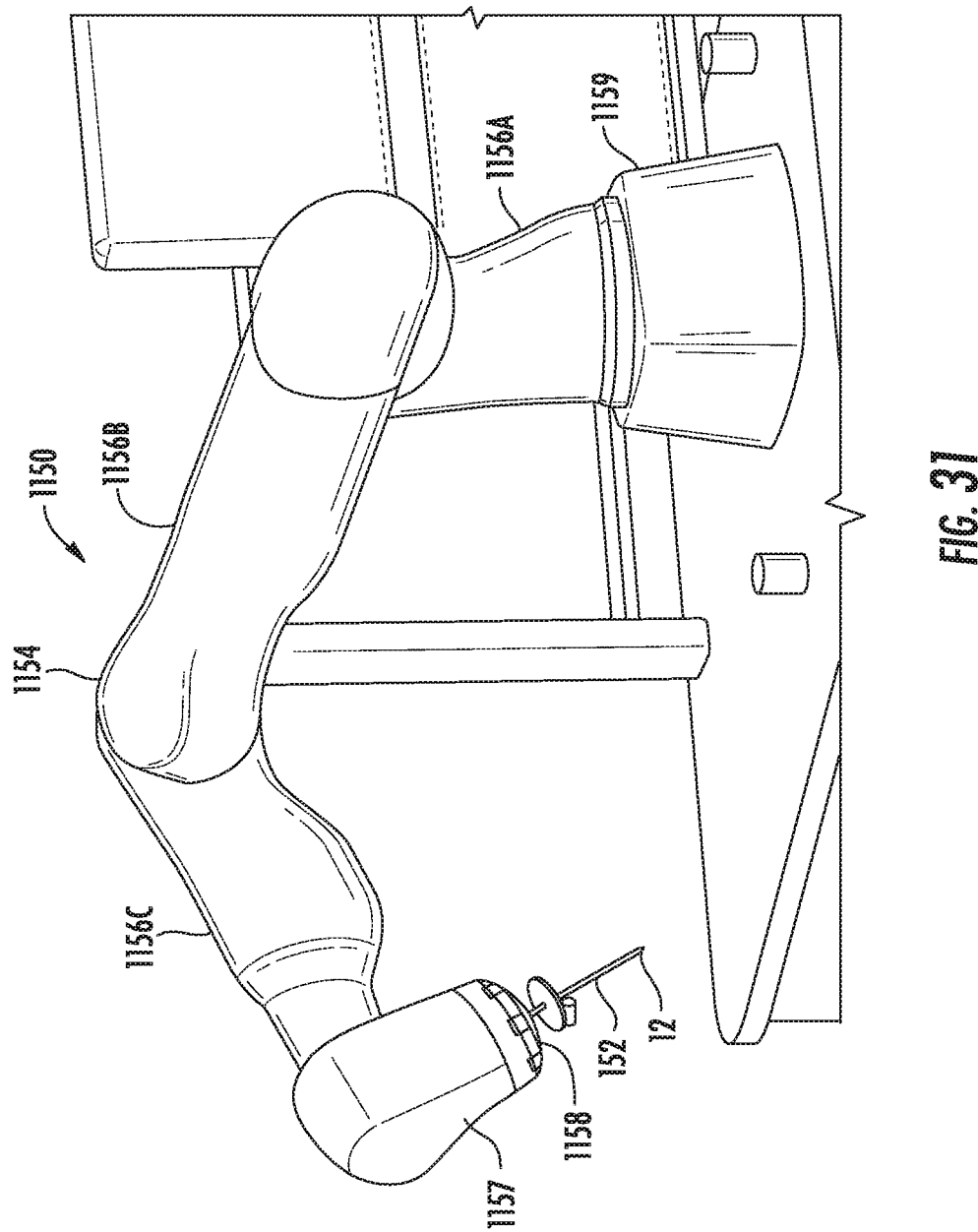
FIG. 31 illustrates the surgical anchor insertion tool with horizontal spool, with the handle removed, attached to a robot/robotic arm.

Each of the sensor anchor delivery tools described herein are configured to allow a user to deliver the surgical sensor anchor 12 or 54 to the required portion of the body in need of a surgical procedure. FIG. 29 illustrates the use of the surgical anchor insertion tool 92 to deliver the surgical anchor 12 to one or more vertebral bodies 238 of the spinal cord 240. FIG. 30 illustrates the insertion of multiple surgical sensor anchors 54, each with an electrical wire 15 attached thereto, to independent vertebral bodies, 238. In addition to being utilized by a human user, i.e. a surgeon, the surgical sensor anchor delivery tools can be adapted to be used by a surgical robot. FIG. 31 illustrates the surgical anchor insertion tool with horizontal spool 152 with the handle removed, attached to a surgical robot 1150. Preferably, the robot(s) 1150 is a mini robot so multiple robots 1150 can be used simultaneously. While only one robot 1150 is shown, it is to be understood that a plurality of robots can be used. Such surgical robots are well known in the art and have multiple axes of freedom, for example, six or seven axes of freedom. The robot 1150 includes a base 1159 and an arm, designated generally 1154, which is comprised of a plurality of relatively movable sections 1156A-1156C and a head 1157. The head 1157 has a free end portion 1158 that is configured to hold various end effectors and/or manipulators, such as tools and grippers, or as shown, an anchor 12. The base 1159 is provided to support the arm portions 1156A-1156C and the head 1157. While an anchor 12 is shown as being manipulated by the robot 1150, it is to be understood that other tools, such as a gripper, can be mounted to the head 1157 for gripping and/or manipulating an anchor 12, 54, or to grip a bone fragment directly for manipulation by the robot 1150.

Figure 32:
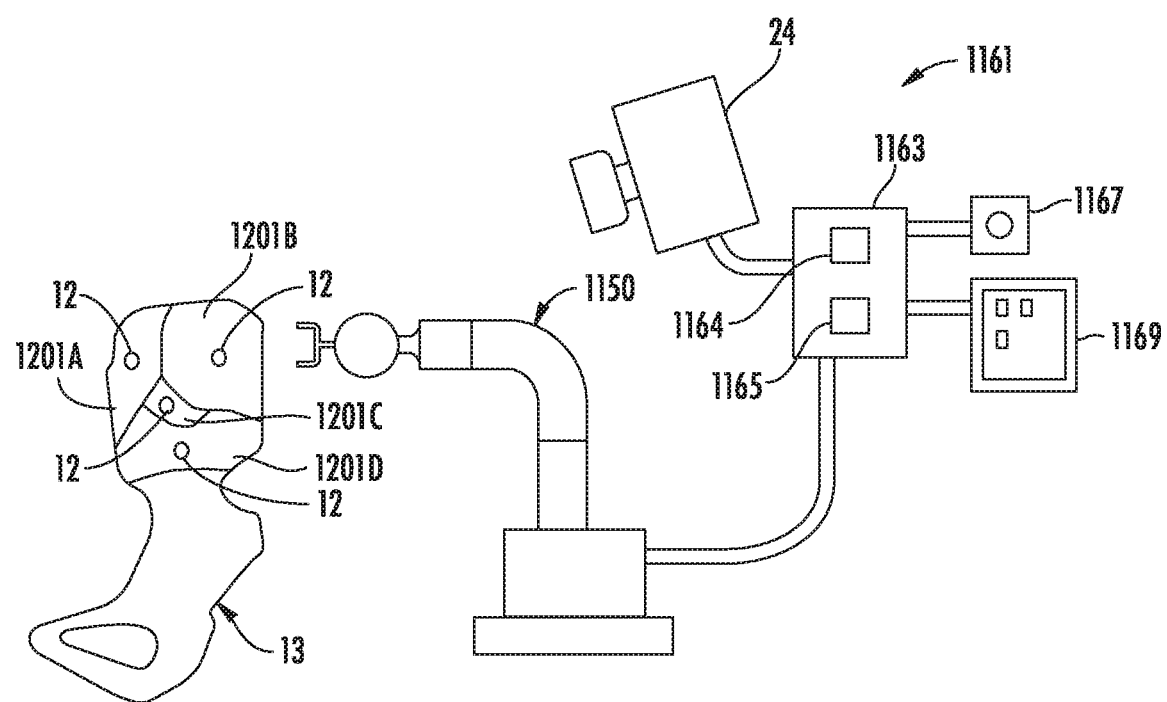
FIG. 32 is a schematic illustration of a robotic surgery system including a surgical robot, a computer system, and a vision system connected to the computer system.

The surgical system, designated generally 1161 and illustrated in FIG. 32, includes at least one robot 1150, a computer 1163 having a memory 1164, and a processor 1165, and is preferably a digital computer. The surgical system 1161 also includes a manually operated controller, such as a telemanipulator 1167, for use by a surgeon or other medical personnel. The surgical system 1161 also includes a display device 1169, such as a touch screen monitor. The surgical system 1161 also includes the visualization system 24. The visualization system 24, controller 1167, display 1169 and robot 1150 are operably connected together via the computer 1163. The computer 1163 is programmed to effect the following described functions.

When performing surgery on a skeletal component, such as a pelvis 13, the surgical site is exposed as is known in the art. The visualization system 24 can be used to create an image of the surgical site to provide an image thereof on the display 1169 to determine the degree of damage and the location of the various fragments, such as the fragments 1201A-1201D. If needed, one or more of the robots 1150 can be used to install anchors 12, 54, or to grip a fragment with a suitable gripping device, such as a pair of jaws mounted to one or more of the robots 1150. The selection of the use of an anchor or a gripping device can be determined by the surgeon and/or the computer 1163 in accordance with the computer programming. Depending on the type of scan of the surgical area to be made, the scan can be accomplished prior to opening the surgical site and/or after opening the surgical site as instructed by the surgeon. The computer 1163 can be programmed to process the information from the scan to determine how the various skeletal fragments are to be repositioned for reconstruction of the broken skeletal component, such as a pelvis. The computer 1163 can be programmed to at least initially determine whether the skeletal component will be gripped with a gripping device or have an anchor installed therein. An image from the scan can be displayed on the display device 1169 to provide information to the surgeon or other medical personnel. The computer 1163 can also be programmed to determine which fragment 1201 goes in which position relative to the other fragments. The moving of the fragments 1201A-1201D into their appropriate positions for reconstruction can be done robotically and/or by the surgeon or other medical personnel.

Additionally, the surgeon can manually control a robot 1150 to move a tool into position to grip a fragment, either by gripping the fragment itself or an anchor 12 as described above. The surgeon can manually move a fragment 1201 into its appropriate position through the controller 1167, through a touchscreen on the display 1169, or by manual manipulation of the robot 1150. The robot 1150 can then be instructed by the surgeon or other medical personnel to maintain that position, i.e. the robot can learn from the instruction what its function should be; for example, hold the fragment in place or move the fragment to another position. This can be done via the controller 1167 or a touchscreen 1169. Further, control elements such as an input switch can be provided on the robot 1150 to assist in instructing the robot 1150 what to do, which would then be controlled by the computer 1163. Fragment identification can be through the sensor 14 embedded in an anchor 12, 54 as described above. It is to be noted that the reconstruction process can utilize more than one robot 1150 simultaneously and independently at one time. It is also to be understood that more than one medical personnel can be utilized to effect operation of the surgical system 1161. For example, the surgeon could move a fragment into place and instruct other personnel to instruct the computer 1161 to learn. Learning can utilize more than one instruction, for example, a first instruction would be to learn and a second instruction would be to hold in place. Visualization can be at the beginning of the surgical process, intermittently during the surgery, or continuously throughout the surgery.

Once the fragments are properly positioned, the robot or robots 1150 can maintain the fragments in their appropriate position while the surgeon can secure the fragments in place with either screws, adhesive or other means, as is well known in the art. Alternatively, additional robots can connect the bone fragments utilizing bone plates, screws and the like.

After the reconstruction, the surgical site can be closed. Also, the visualization can include a scan of the completed reconstruction.

Figure 33:
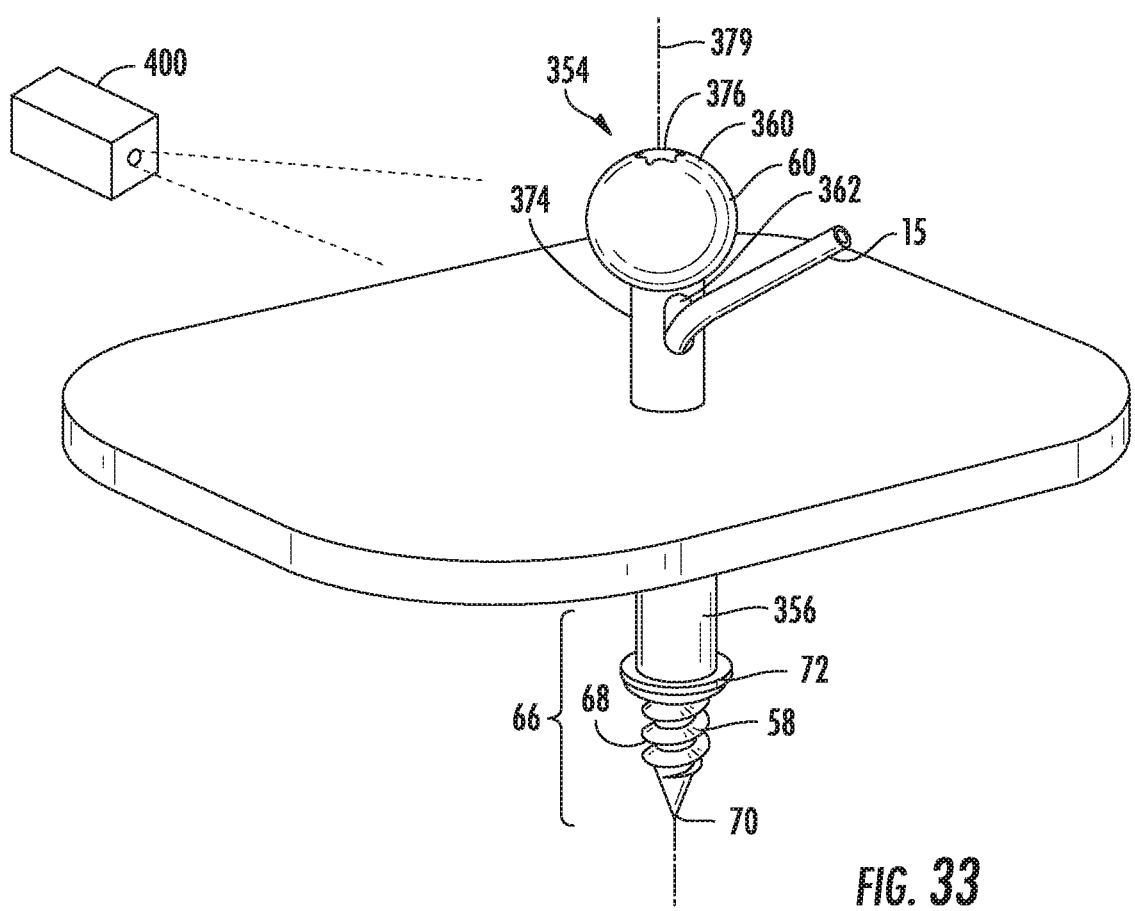
FIG. 33 illustrates an optical marker that is used in combination with an inspection camera to monitor movement of the optical marker.

FIG. 33 illustrates an alternative embodiment of the anchor for use in a surgical procedure, which may be configured to house a sensor therein, referred to generally as a surgical sensor anchor 354. The surgical sensor anchor 354 comprises a main body 356 having a first end 58 configured to engage with a body part or organ, such as a vertebra, and an opposing second end 60 positioned away from the body part when inserted therein. While the main body 356 is shown having a generally tubular shape, such shape is illustrative only and not limiting. The second end 60 includes a geometric shape 360. The geometric shape 360 is sized and shaped to include a surface finish configured to cooperate with an inspection camera 400 secured in close proximity to the anchor. The inspection camera is of the type typically utilized for inspecting production line parts in real time. Such inspection systems are currently utilized for determining part orientation, tolerance monitoring and part presence, and are manufactured by at least ATS Automation, 730 Fountain St. N., Building #2, Cambridge ON. N3H 4R7 Canada. These cameras typically use pixel differentiation, contrast algorithms, or the like, to determine the size of a part as it's viewed by the camera from a fixed distance. This type of inspection camera system is modified from its typical inspection use to track movement of the part in place of one of the typical functions, such as part tolerance monitoring. Movement, including orientation and yaw of the geometric shape, is monitored to determine how far the anchor 354, and thus the body part, has moved or rotated. In at least one embodiment, the anchor 354 is provided with an opening 362 sized to allow the sensor 14 to be inserted into and stored within an interior region 64 of the surgical sensor anchor 354. In addition to the electromagnetic sensors 14, small gyroscopes or inertia sensors, such as those found in cell phones, may be inserted into the hollow shank of the anchor 354. The first end 58 of the surgical sensor anchor 354 may contain an initial insertion portion 66 constructed to aid in insertion into, for example, a vertebra. A threaded portion 68 allows the surgical sensor anchor 354 to be screwed into and secured to the vertebra or other anatomical structure. The insertion portion 66 terminates in an initial body part engaging portion, illustrated herein as a sharp or pointed tip 70. At, near, or extending from the first end 58, preferably prior to the threaded portion 68, is a circumferential flange 72. The circumferential flange 72 is illustrated having a generally circular shape or profile and extending around a perimeter of the surgical sensor anchor 354 main body 356.

Positioned along the outer surface 374 of the main body 356 is an insertion tool engaging aperture 376. The insertion tool engaging aperture 376 is illustrated herein as a non-limiting TORX drive and arranged in a generally parallel orientation relative to the surgical anchor longitudinal axis 379. It should be noted that the TORX driver is illustrated; however, any inwardly or outwardly extending shape suitable for inserting the anchor into the anatomy could be substituted without departing from the scope of the art.

Figure 34:
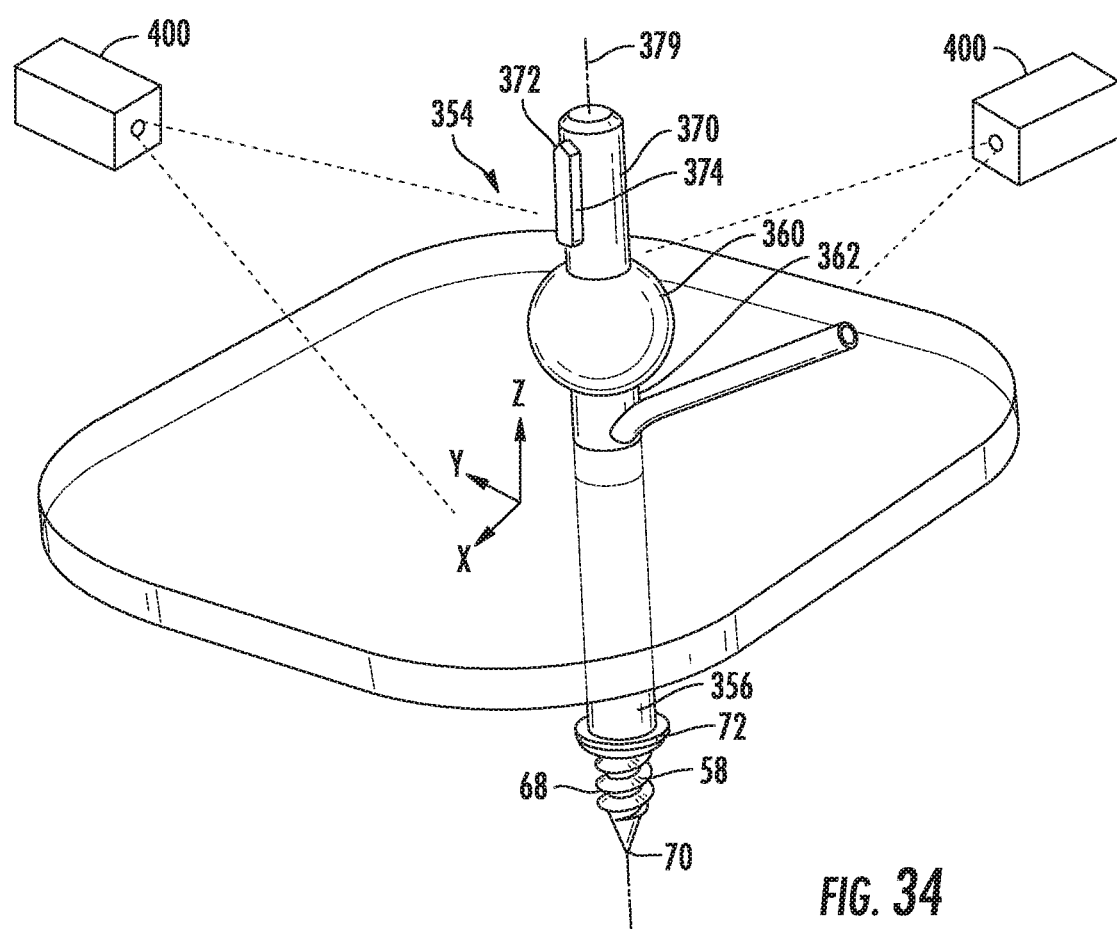
FIG. 34 illustrates an alternative version of the optical marker; this optical marker includes a secondary shape which may be monitored by the same or a secondary inspection camera to monitor movement of the optical marker in multiple planes.
Figure 35:
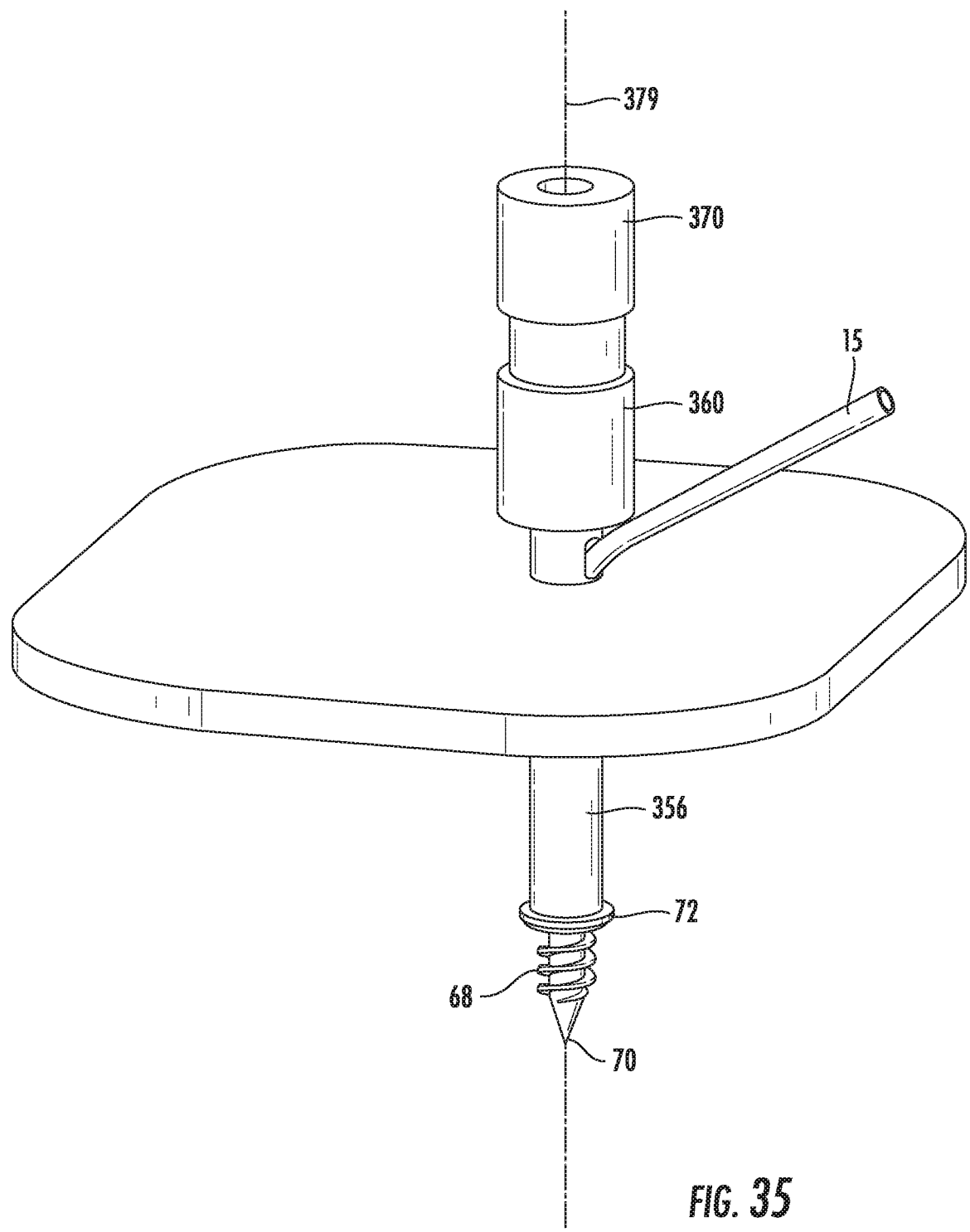
FIG. 35 illustrates the surgical sensor anchor with variously shaped geometric shape and secondary geometric shape.

Referring to FIG. 34, an alternative embodiment of the surgical sensor anchor 354 is illustrated. This embodiment includes an outwardly extending secondary geometric shape 370 that may also be monitored by one or more cameras 400 to provide additional axes of monitoring. The secondary geometric shape 370 preferably includes a protuberance shape 372 that allows for the camera to monitor rotation and yaw angle of the anchor about the longitudinal axis 379 in addition to the X, Y and Z monitoring provided by geometric shape 360, and thus the anatomy to which it is attached. The protuberance shape also allows for insertion of the anchor by providing a driving surface 374. It should also be noted that a single shaped surface in combination with a single inspection camera 400 can be used to measure up to six (6) degrees of freedom of movement by modifying or combining geometric shapes. An example of such a shape is parallelepiped or cylindrical. FIG. 35 illustrates the surgical sensor anchor 354 in which the geometric shape 360 and the secondary geometric shape 370 are both cylindrical. Although not illustrated, an embodiment of the surgical sensor anchor 354 may include just the geometric shape 360 having a shape that is not round, such as cylindrical.

The sensor control system 27 preferably includes one or more sensor control modules. Each sensor control module is a software-based interactive processing program that interacts with surgical personnel through a graphical user interface presented on an output display device. The sensor control module allows a user to create and store positions, e.g. define, sensor anchors as fiducial markers with respect to known fiducial points of the patient's anatomy, and particularly the skeletal structure. To monitor the stored positions, the sensor control module may include a boundary definition function that allows the user to define a boundary around the fiducial marker and sensor anchors, and may additionally hide extraneous image data that is outside the bounded area. In this manner, the user can define a boundary for movement of the fiducial marker that may trigger alarms, stop the surgical procedure for realignment or recalibration, or may adjust the positioning and movements of the robot(s) to compensate for the monitored movement of the anatomy.

Figure 36:
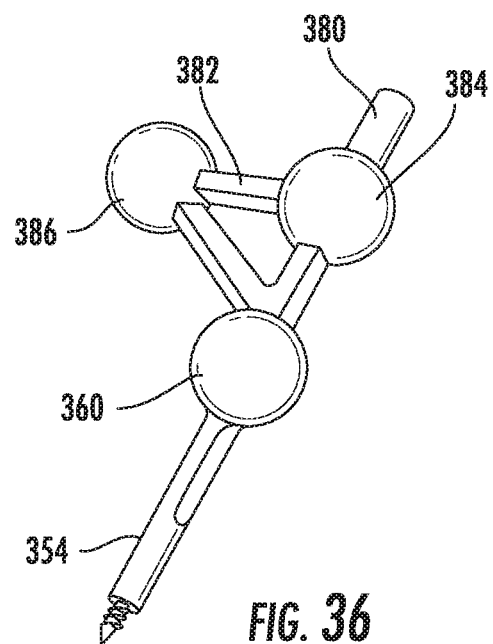
FIG. 36 is a perspective view of the surgical sensor anchor with an antenna fiducial.
Figure 37:
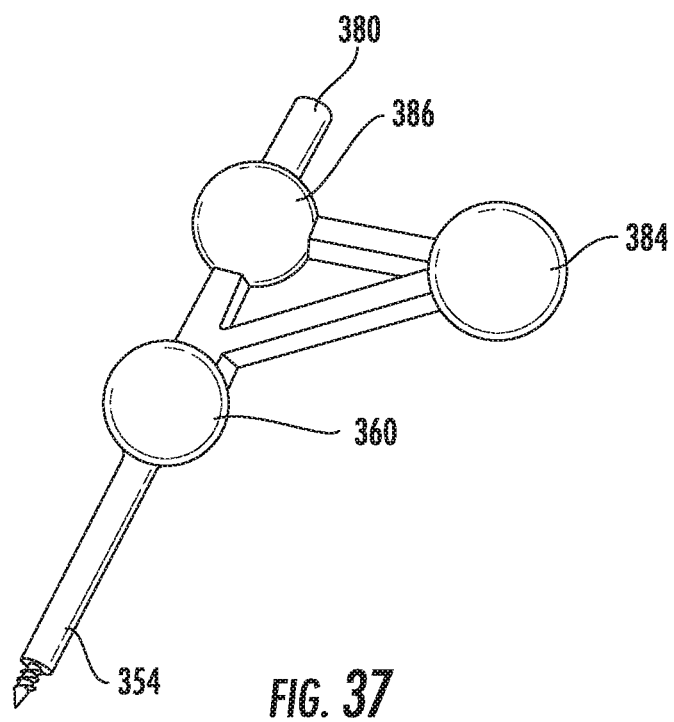
FIG. 37 is an alternative perspective view of the surgical sensor anchor with an antenna fiducial shown in FIG. 36.

FIGS. 36 and 37 illustrate an embodiment of the surgical sensor anchor 354 which comprises an antenna fiducial 380. The antenna fiducial 380 may contain a support structure 382 and two or more geometrical shapes, 384 and 386. Geometric shape 384 and geometric shape 386 are sized and shaped to include a surface finish configured to cooperate with an inspection camera 400 secured in close proximity to the anchor and can be used to measure up to six (6) degrees of freedom of movement. As shown, geometric shape 384 and geometric shape 386 are orientated in a generally linear manner, or at least in the same plane. Geometric shape 384 and geometric shape 360 are also orientated in a generally linear manner, or at least in the same plane. Relative to geometric shape 360, geometric shape 386 is oriented in a different plane and is off center from surgical anchor longitudinal axis 379. The antenna fiducial 380 may be permanently attached. Alternatively, the antenna fiducial 380 may be configured to be removably attached. In this manner, the antenna fiducial 380 can be left in for use in measuring various degrees of freedom of movement or removed for single geometric shape sensing.

Figure 38:
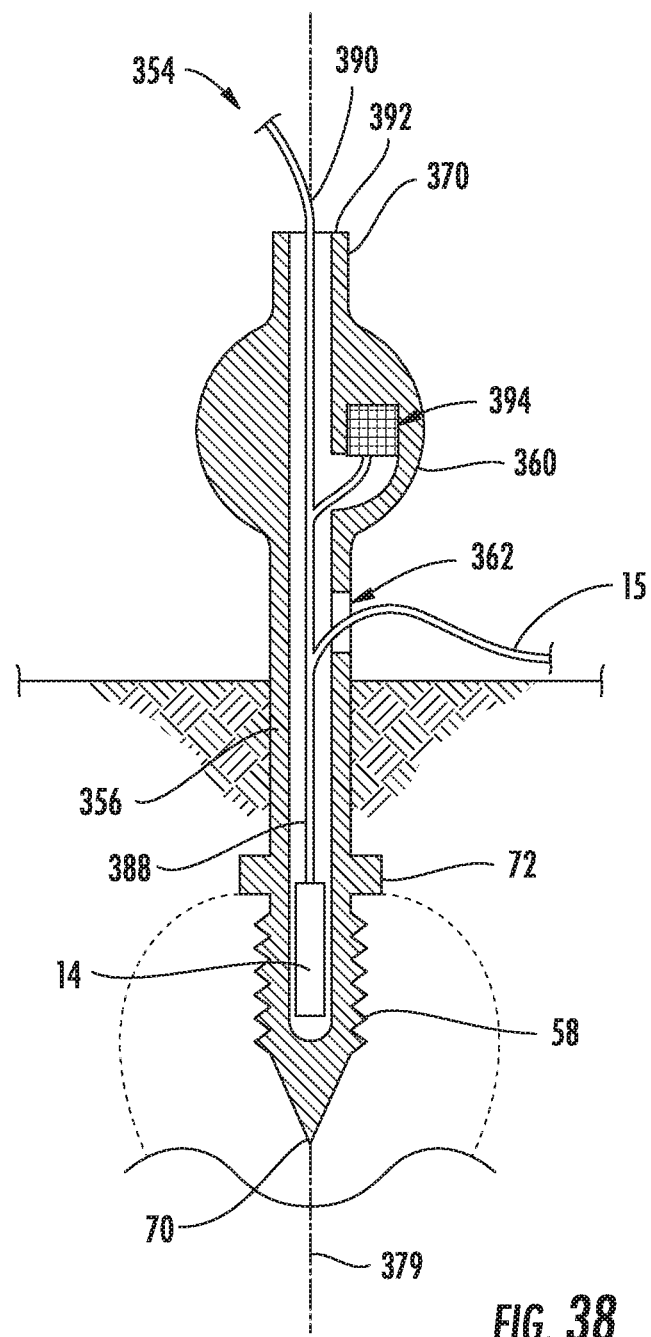
FIG. 38 is a cross sectional view of the embodiment of the surgical sensor anchor illustrated in FIG. 33.

FIG. 38 is a cross sectional view of the embodiment of the surgical sensor anchor 354 illustrated in FIG. 33, taken along the surgical anchor longitudinal axis 379, with geometric shape 360 and second geometric shape 370. The internal lumen or area 388 is shown housing sensor 14 and primary sensor wire 15 (out through port 362) and optionally a secondary electrical wire 390, (out through optional secondary wire port 392. The surgical sensor anchor 354 may include an optional secondary sensor(s) 394, to provide for both electromagnetic (14) and optical (394) sensing, such as an accelerometer sensor, an ultrasound sensor, or multiple sensors, such as a combination of accelerometer and ultrasound sensors.

Figure 39:
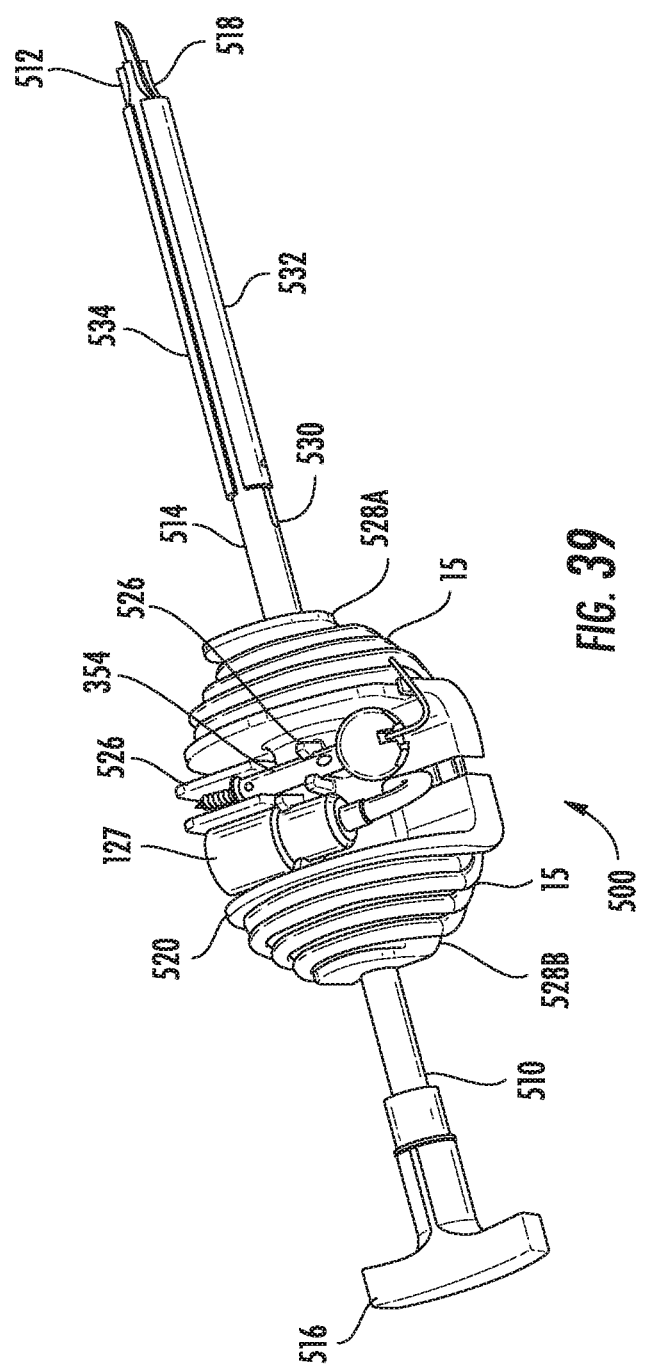
FIG. 39 is a perspective view of an alternative embodiment of the anchor delivery tool.
Figure 40:
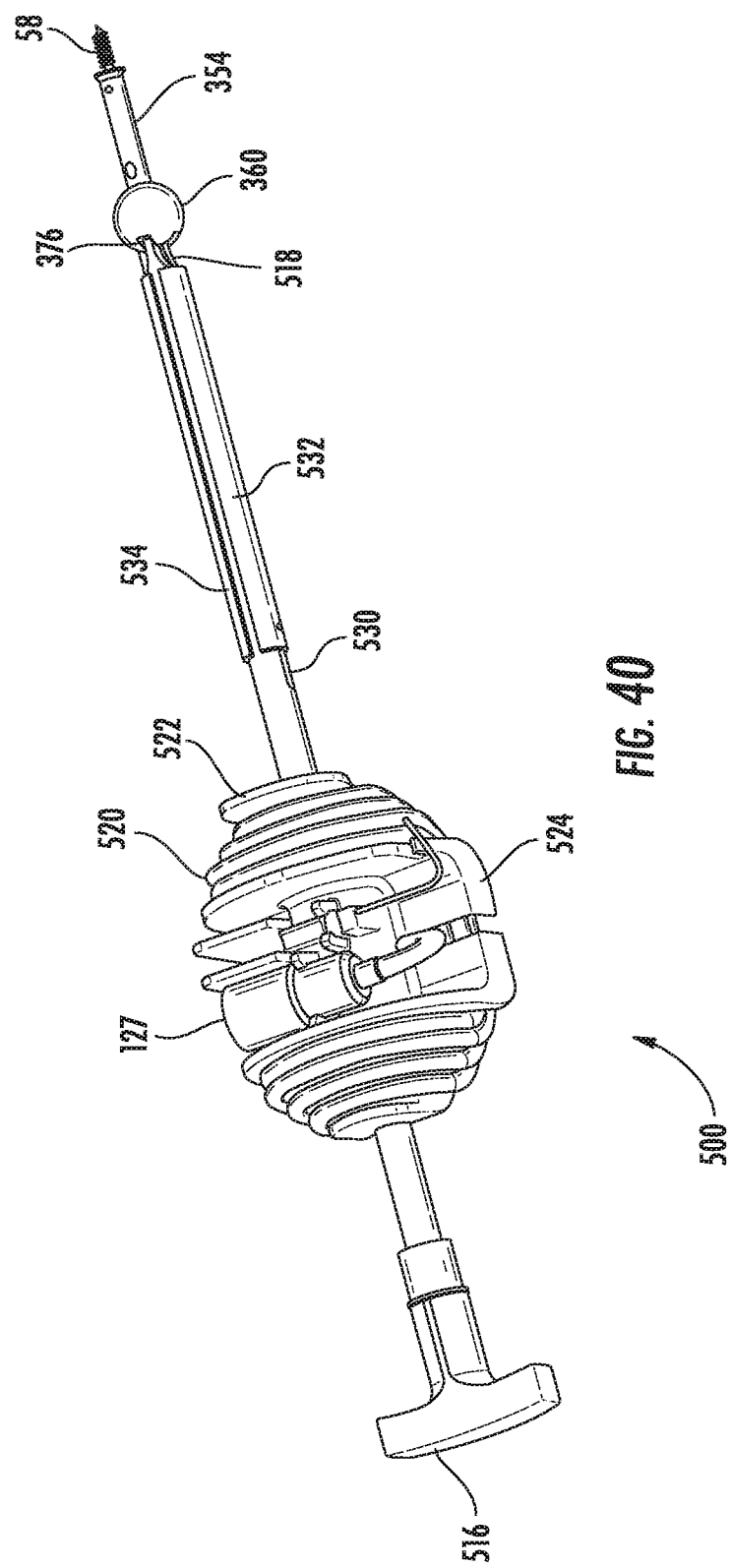
FIG. 40 is an alternative perspective view of the the anchor delivery tool shown in FIG. 39.
Figure 41:
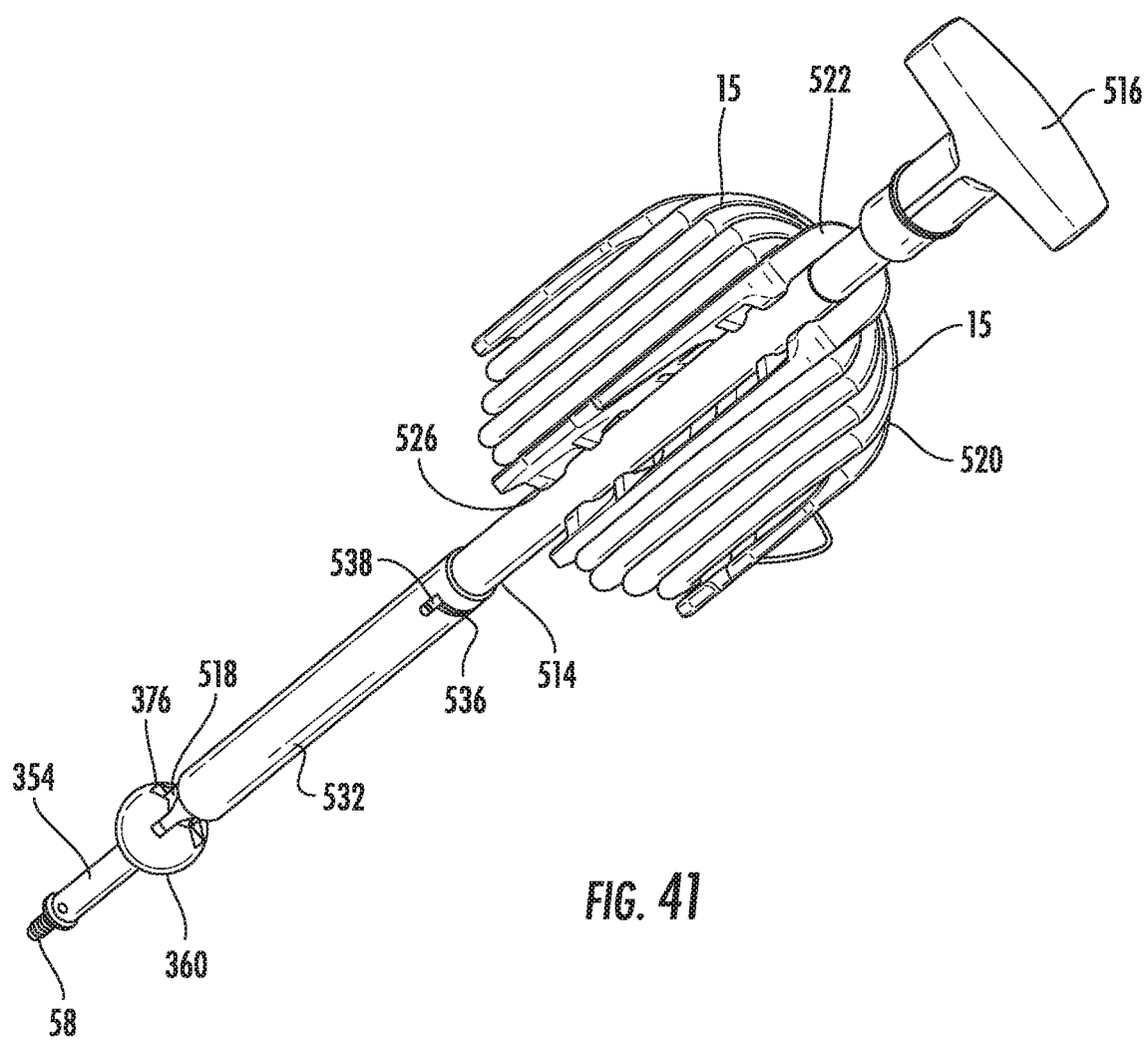
FIG. 41 is an alternative perspective view of the anchor delivery tool shown in FIG. 39.

FIGS. 39-41 illustrate an alternative embodiment of the anchor delivery tool, referred to generally as surgical anchor insertion tool with ball shaped spool 500, shown adapted to interact with the surgical sensor anchor 354. The surgical anchor insertion tool with ball shaped spool 500 comprises a first end 510, a second end 512, and a main body shaft 514. A handle 516, shown as a T-shaped handle, is attached to or integrally formed to the first end 510. The second end 512 includes surgical anchor engaging member 518. The surgical anchor engaging member 518 is configured to receive and secure the surgical sensor anchor 354 (or sensor anchor 12/54) thereto. In this embodiment, the surgical anchor engaging member 518 is sized and shaped to fit within or engage with at least a portion of the surgical sensor anchor 354, preferably the insertion tool engaging aperture 376, see FIGS. 40 and 41. Attached to at least a portion of the main body shaft 514 is a ball shaped spool 520. The ball shaped spool 520 comprises a support frame 522 which is sized and shaped to engage with and secure to at least a portion of the main body shaft 514. The ball shaped spool 520 contains a main compartment 524 having various securing members, illustrated herein as clasp cradle prongs 526 for securing the surgical sensor anchor 354 or the sensor connector 127 in place. Secondary compartments 528A and 528B can be used to store or secure the sensor electrical wire 15. The main body shaft 514 contains a slot 530 which allows the sensor electrical wire 15 to remain in place. Sleeve 532, surrounding a portion of the main body shaft 514 contains a slotted opening 534. The sleeve 532 maintains the sensor electrical wire 15 in place during attachment of the surgical sensor anchor 354. Rotation of the sleeve 532 allows the sensor electrical wire 15 freedom to be moved away from the main body shaft 514. Sleeve 532 may be locked in place via a sleeve locking member, illustrated herein as sleeve slot 536 and pin 538.

All patents and publications mentioned in this specification are indicative of the levels of those skilled in the art to which the invention pertains.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A surgical sensor anchor system for use in surgical procedures utilizing robotic devices comprising:
   a surgical sensor anchor, said surgical sensor anchor comprising:
   a first end configured to engage with a body part or organ;
   an opposing second end positioned at a distance from said body part when inserted therein; and
   a main body having a tubular shape, said tubular shape having an outer surface, said main body separating said first end and said second end, said tubular shape of said main body having an interior region and an insertion tool engaging member positioned on said outer surface and configured for engaging with a surgical anchor insertion tool member;
   an electromagnetic sensor, said electromagnetic sensor housed within said interior region of said main body, and being connected to a sensor wire extending out of said second end of said main body, said sensor wire being placed within said surgical anchor insertion tool member during insertion, wherein a portion of said electromagnetic sensor is positioned below an outer surface of a bone when said main body is engaged to said bone.

2. The surgical sensor anchor system for use in surgical procedures utilizing robotic devices according to claim 1, further including a robot with software to drive robotic functionality.

3. The surgical sensor anchor system for use in surgical procedures utilizing robotic devices according to claim 2, further including visualizing equipment.

4. The surgical sensor anchor system for use in surgical procedures utilizing robotic devices according to claim 3, further including a sensor control system.

5. The surgical sensor anchor system for use in surgical procedures utilizing robotic devices according to claim 1, wherein said sensor tracks six degrees of movement.

6. The surgical sensor anchor system for use in surgical procedures utilizing robotic devices according to claim 1, wherein said sensor provides feedback data to a robot, wherein said feedback data provided causes said robot to either move or to hold in position for securement in proper place.

7. The surgical sensor anchor system for use in surgical procedures utilizing robotic devices according to claim 6, wherein said feedback data provided causes said robot to adjust position or movement in real-time, or stop a movement until additional input is performed.

8. The surgical sensor anchor system for use in surgical procedures utilizing robotic devices according to claim 1, wherein said surgical sensor anchor first end comprises a threaded portion.

9. The surgical sensor anchor system for use in surgical procedures utilizing robotic devices according to claim 1, wherein said surgical sensor anchor comprises a geometric shape.

10. The surgical sensor anchor system for use in surgical procedures utilizing robotic devices according to claim 9, wherein said surgical sensor anchor comprises a secondary geometric shape.

11. The surgical sensor anchor system for use in surgical procedures utilizing robotic devices according to claim 9, wherein said surgical sensor anchor comprises an antenna fiducial.

12. The surgical sensor anchor system for use in surgical procedures utilizing robotic devices according to claim 1, further including at least one secondary sensor, wherein said at least one secondary sensor is an accelerometer sensor or an ultrasound sensor.

13. The surgical sensor anchor system for use in surgical procedures utilizing robotic devices according to claim 1, wherein said insertion tool engaging member includes an elongated member arranged in a generally parallel orientation relative to an anchor longitudinal axis.

14. The surgical sensor anchor system for use in surgical procedures utilizing robotic devices according to claim 13, wherein said insertion tool engaging member comprises an elongated member having an angled or ramped surface for guiding the surgical anchor insertion tool member.

15. The surgical sensor anchor system for use in surgical procedures utilizing robotic devices according to claim 1, wherein said main body includes a circumferential flange.

16. The surgical sensor anchor system for use in surgical procedures utilizing robotic devices according to claim 1, wherein said main body comprises an interior region sized and shaped for said sensor to be inserted and stored therein.

17. The surgical sensor anchor system for use in surgical procedures utilizing robotic devices according to claim 1, wherein at least half of said electromagnetic sensor is positioned below said outer surface of said bone when said main body is engaged to said bone.

18. The surgical sensor anchor system for use in surgical procedures utilizing robotic devices according to claim 1, wherein all of said electromagnetic sensor is positioned below said outer surface of said bone when said main body is engaged to said bone.

19. The surgical sensor anchor system for use in surgical procedures utilizing robotic devices according to claim 1, wherein said second end of said body portion includes an opening, said opening having a diameter sufficient to allow the sensor to be inserted into and stored within an interior region of said surgical sensor anchor.

20. The surgical sensor anchor system for use in surgical procedures utilizing robotic devices according to claim 1, wherein said first end of said surgical sensor anchor includes an initial insertion portion constructed to aid in insertion into said bone, said insertion portion terminating in a pointed tip.

21. The surgical sensor anchor system for use in surgical procedures utilizing robotic devices according to claim 1, wherein said outer surface of said main body includes at least one helical thread.

22. The surgical sensor anchor system for use in surgical procedures utilizing robotic devices according to claim 1, wherein said outer surface of said main body includes a circumferential flange, said circumferential flange having a generally circular shape and extending around a perimeter of said surgical sensor anchor main body to establish a desired depth that said electromagnetic sensor extends below said outer surface of said bone.

* * * * *